(12) United States Patent
Yamauchi et al.

(10) Patent No.: US 10,422,622 B2
(45) Date of Patent: Sep. 24, 2019

(54) INTERFERENCE OPTICAL DEVICE, INTERFERENCE OBSERVATION DEVICE, AND INTERFERENCE OBSERVATION METHOD

(71) Applicant: HAMAMATSU PHOTONICS K.K., Hamamatsu-shi, Shizuoka (JP)

(72) Inventors: Toyohiko Yamauchi, Hamamatsu (JP); Hidenao Yamada, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 120 days.

(21) Appl. No.: 15/546,126

(22) PCT Filed: Dec. 14, 2015

(86) PCT No.: PCT/JP2015/084918
§ 371 (c)(1),
(2) Date: Jul. 25, 2017

(87) PCT Pub. No.: WO2016/121249
PCT Pub. Date: Aug. 4, 2016

(65) Prior Publication Data
US 2018/0017370 A1    Jan. 18, 2018

(30) Foreign Application Priority Data
Jan. 30, 2015    (JP) ................................. 2015-016267

(51) Int. Cl.
*G01B 9/02*    (2006.01)
*G02B 21/00*    (2006.01)
(Continued)

(52) U.S. Cl.
CPC .......... *G01B 9/0203* (2013.01); *G01N 21/45* (2013.01); *G02B 21/0056* (2013.01);
(Continued)

(58) Field of Classification Search
CPC ........... G01B 9/02027; G01B 9/02028; G01B 9/0203; G01B 9/02041; G01B 9/02049;
(Continued)

(56) References Cited

U.S. PATENT DOCUMENTS 5,133,601 A * 7/1992 Cohen ................ G01B 11/2441
250/559.22
6,084,672 A * 7/2000 Lewin ...................... G01B 9/04
356/496
(Continued)

FOREIGN PATENT DOCUMENTS

JP    2002-311333 A    10/2002
JP    2009-116082 A    5/2009
(Continued)

OTHER PUBLICATIONS

International Preliminary Report on Patentability dated Aug. 10, 2017 for PCT/JP2015/084918.

*Primary Examiner* — Michael A Lyons
(74) *Attorney, Agent, or Firm* — Drinker Biddle & Reath LLP

(57) ABSTRACT

An interference observation apparatus includes an interference optical apparatus, a microscope housing, an imaging unit, and an objective lens. The interference optical apparatus includes a housing, a light source, a photodetector, beam splitters, a reference mirror, and a control unit. The interference observation apparatus is configured such that the housing of the interference optical apparatus is disposed between the objective lens attachment portion and the objective lens in a microscope apparatus including the imaging unit for capturing an image of the light passing through the objective lens attached to the objective lens attachment portion having an opening.

23 Claims, 14 Drawing Sheets

(51) Int. Cl.
*G02B 21/14* (2006.01)
*G01N 21/45* (2006.01)
*G02B 21/36* (2006.01)

(52) U.S. Cl.
CPC .......... *G02B 21/14* (2013.01); *G01B 9/02041* (2013.01); *G02B 21/362* (2013.01)

(58) Field of Classification Search
CPC ............ G01B 9/02051; G01B 9/02052; G01B 9/02067; G01B 9/04; G01N 21/45; G02B 21/0056; G02B 21/14; G02B 21/362
See application file for complete search history.

(56) References Cited

U.S. PATENT DOCUMENTS

| | | | |
|---|---|---|---|
| 6,657,728 B1* | 12/2003 | Okabe | G01B 9/02049 356/450 |
| 6,940,602 B2* | 9/2005 | Dubois | G02B 21/00 356/497 |
| 2008/0018966 A1 | 1/2008 | Dubois et al. | |
| 2010/0231895 A1 | 9/2010 | Mann et al. | |
| 2012/0184846 A1* | 7/2012 | Izatt | G02B 21/0012 600/425 |
| 2013/0182096 A1* | 7/2013 | Boccara | A61B 5/0066 348/79 |
| 2016/0143589 A1* | 5/2016 | Kabetani | A61B 5/702 600/476 |

FOREIGN PATENT DOCUMENTS

| | | |
|---|---|---|
| JP | 2009/122033 A | 6/2009 |
| JP | 2010-139326 A | 6/2010 |
| JP | 2015-503128 A | 1/2015 |
| WO | WO-2013/095282 A2 | 6/2013 |

\* cited by examiner

Fig.10
(a)
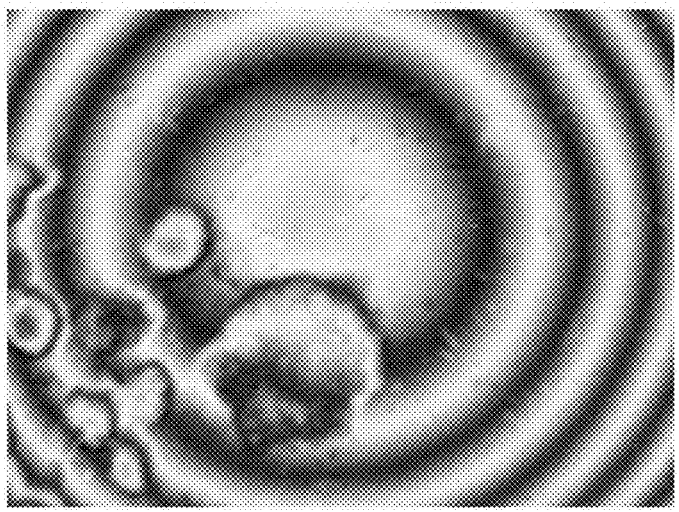
(b)
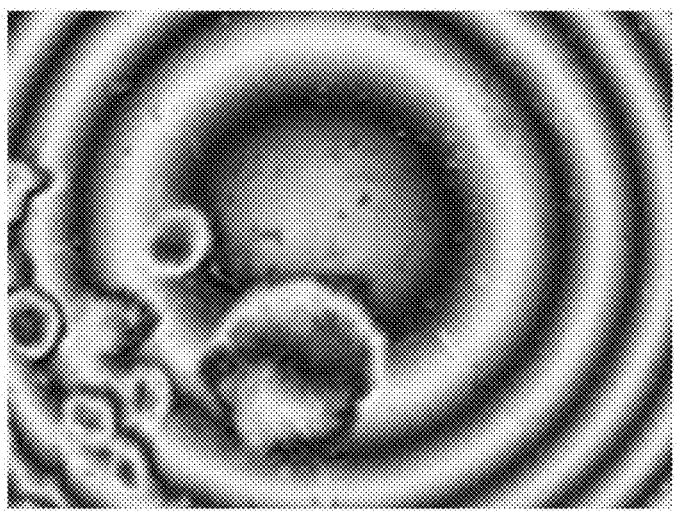

*Fig.11*
(a)
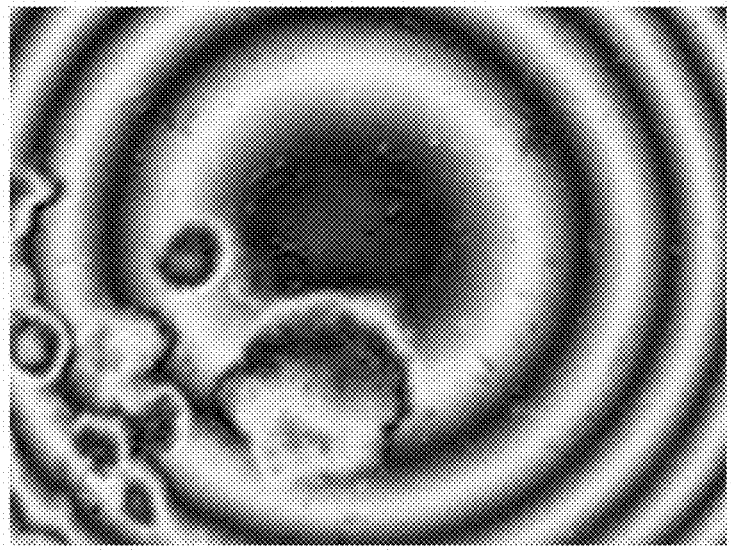
(b)

INTERFERENCE OPTICAL DEVICE, INTERFERENCE OBSERVATION DEVICE, AND INTERFERENCE OBSERVATION METHOD

TECHNICAL FIELD

The present invention relates to an interference optical apparatus, an interference observation apparatus including the interference optical apparatus, and an interference observation method using the interference optical apparatus.

BACKGROUND ART

Patent Document 1 discloses an interference observation apparatus which acquires an interference image of an observation object. This interference observation apparatus, using an optical system of a Michelson interferometer, splits incoherent light output from a first light source into first split light and second split light, reflects the first split light by the observation object, combines the first split light and the second split light, and acquires an image of interference light generated by the combining.

Further, the interference observation apparatus performs feedback control on an optical path difference between two optical paths in the Michelson interferometer on the basis of a detection result of the interference light using a second light source which outputs coherent laser light.

Here, a technique of keeping the optical path difference constant between two optical paths in the interferometer by the feedback control on the basis of the interference light detection result is called "phase lock". A technique of changing a value of the optical path difference kept by the phase lock using the feedback control is called "phase shift".

CITATION LIST

Patent Literature

Patent Document 1: Japanese Patent Application Laid-Open No. 2009-122033

SUMMARY OF INVENTION

Technical Problem

In the interference observation apparatus disclosed in Patent Document 1, it is not easy to make the optical adjustment when individual components are prepared and assembling is performed, and thus the cost is increased.

The present invention has been made in order to solve the above problem, and an object thereof is to provide an interference observation apparatus which can make the optical adjustment easy and be configured at a low cost, an interference optical apparatus which can be suitably used in the interference observation apparatus, and an interference observation method using the interference optical apparatus.

Solution to Problem

An interference optical apparatus according to one aspect of the present invention is an interference optical apparatus to be disposed between an objective lens attachment portion and an objective lens in a microscope apparatus including an imaging unit for capturing an image of light passing through the objective lens attached to the objective lens attachment portion having an opening, and includes (1) a first attachment portion including an opening to be optically coupled to the opening of the objective lens attachment portion; (2) a second attachment portion including an opening to be optically coupled to the objective lens; (3) a light source for outputting light; (4) a photodetector for receiving combined light and outputting a detection signal; (5) a first beam splitter optically coupled to the light source and the photodetector, for inputting the light output from the light source and outputting the light along a predetermined direction, and inputting the combined light and outputting the combined light to the photodetector; (6) a second beam splitter optically coupled to the first beam splitter, for splitting the light output from the first beam splitter into first split light and second split light, irradiating an observation object with the first split light through the objective lens and inputting the first split light reflected by the observation object, inputting the second split light passing through a reference optical path, combining these input first split light and second split light and outputting the combined light to the opening of the first attachment portion and the first beam splitter; (7) a reference optical system optically coupled to the second beam splitter and provided on the reference optical path, and including a first lens for condensing the second split light output from the second beam splitter, a reference mirror for reflecting the second split light condensed by the first lens to the first lens, and a mirror moving unit for moving the reference mirror in a direction of an optical axis of the first lens; and (8) a housing for holding the first attachment portion, the second attachment portion, the light source, the photodetector, the first beam splitter, the second beam splitter, and the reference optical system.

An interference observation apparatus according to one aspect of the present invention includes a microscope apparatus including an imaging unit for capturing an image of light passing through an objective lens attached to an objective lens attachment portion having an opening; and the above-described interference optical apparatus of the present invention, and the housing of the interference optical apparatus and optical components held by the housing are disposed between the objective lens attachment portion and the objective lens, the objective lens attachment portion and the first attachment portion are optically coupled to each other, and the objective lens and the second attachment portion are optically coupled to each other.

An interference observation method according to one aspect of the present invention includes, in a microscope apparatus including an imaging unit for capturing an image of light passing through an objective lens attached to an objective lens attachment portion having an opening, disposing the above-described interference optical apparatus of the present invention between the objective lens attachment portion and the objective lens, optically coupling the objective lens attachment portion and the first attachment portion to each other, and optically coupling the objective lens and the second attachment portion to each other; obtaining a phase difference in accordance with an optical path difference between the first split light and the second split light from the splitting to the combining in the second beam splitter on the basis of the detection signal, and driving the mirror moving unit on the basis of the obtained phase difference and controlling the optical path difference; and acquiring an interference image using the imaging unit.

Advantageous Effects of Invention

According to one aspect of the present invention, it is possible to make an optical adjustment easy and acquire an interference image of an observation object with an inexpensive configuration.

BRIEF DESCRIPTION OF DRAWINGS

FIG. 10 includes views showing interference images.

FIG. 11 includes views showing interference images.

DESCRIPTION OF EMBODIMENTS

Hereinafter, embodiments for carrying out the present invention will be described in detail with reference to the accompanying drawings. In the description of the drawings, the same elements will be denoted by the same reference signs, without redundant description. The present invention is not limited to these examples, and the Claims, their equivalents, and all the changes within the scope are intended as would fall within the scope of the present invention.

Figure 1:
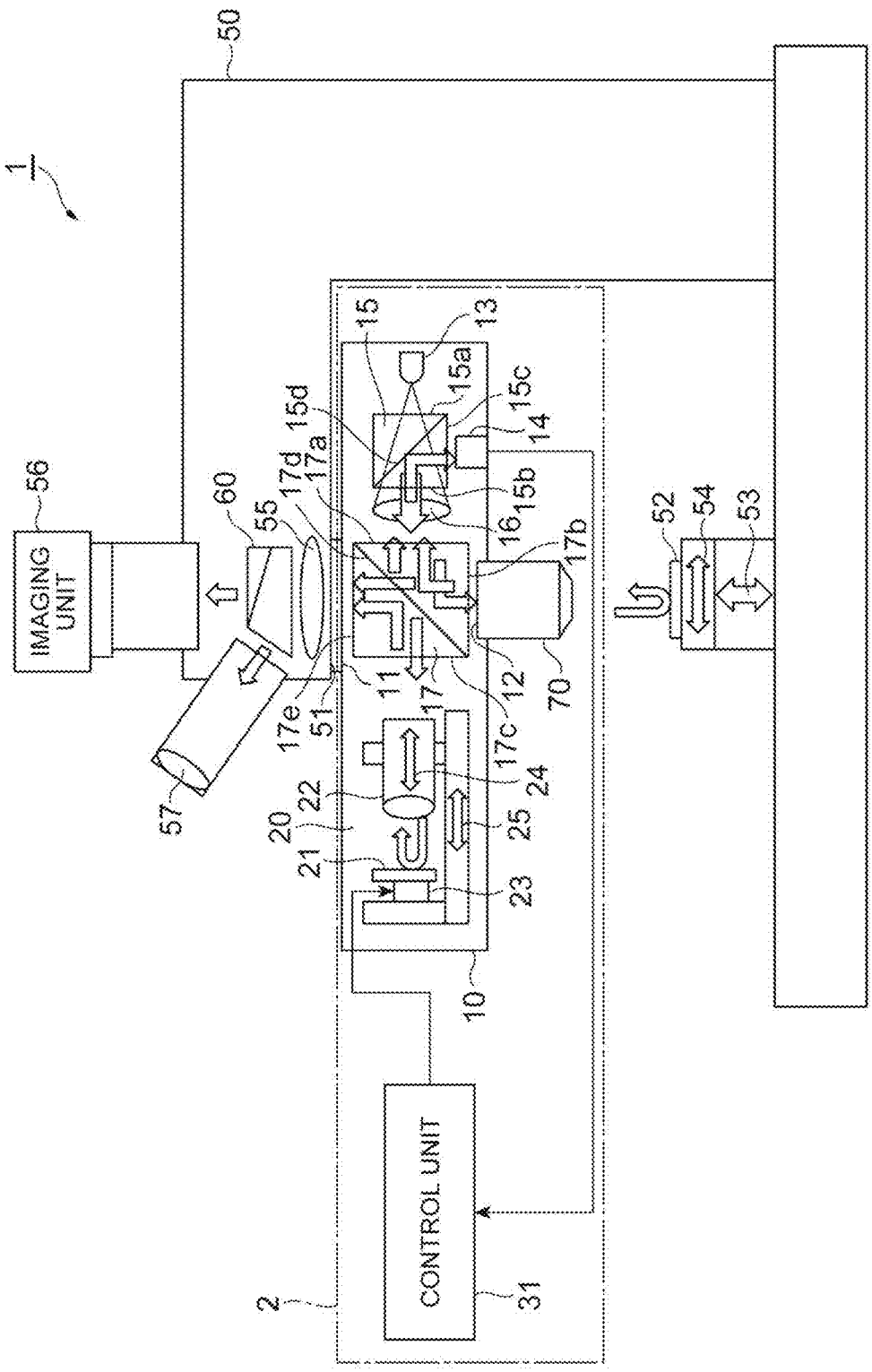
FIG. 1 is a diagram illustrating a configuration of an interference observation apparatus 1.

FIG. 1 is a diagram illustrating a configuration of an interference observation apparatus 1 of the present embodiment. The interference observation apparatus 1 includes an interference optical apparatus 2, a microscope housing 50, an objective lens attachment portion 51, a sample holding table 52, stages 53, 54, a tube lens 55, an imaging unit 56, an eyepiece lens 57, and an objective lens 70. Further, the interference optical apparatus 2 includes a housing 10, a first attachment portion 11, a second attachment portion 12, a light source 13, a photodetector 14, a first beam splitter 15, a second lens 16, a second beam splitter 17, a reference mirror 21, a first lens 22, a drive element 23, stages 24, 25, and a control unit 31.

The interference observation apparatus 1 includes an optical system of the Michelson interferometer, and acquires an interference image on the basis of the light reflected by an observation object held on the sample holding table 52. The observation object is not limited to a specific cell or a biological sample. For example, the observation object includes a cultured cell, an immortalized cell, a primary cultured cell, a cancer cell, a fat cell, a liver cell, a cardiac muscle cell, a nerve cell, a glia cell, a somatic stem cell, an embryonic stem cell, a pluripotential stem cell, an iPS cell, and a cell aggregation (spheroid) created on the basis of at least one of these cells. Further, the observation object is not limited to a biological object, and includes an industrial sample such as a metal surface, a semiconductor surface, a glass surface, an inside of a semiconductor element, a resin material surface, a liquid crystal, and a high molecular compound.

The interference observation apparatus 1 is configured such that the housing 10 of the interference optical apparatus 2 is disposed between the objective lens attachment portion 51 and the objective lens 70 in a microscope apparatus including the imaging unit for capturing an image of the light passing through the objective lens 70 attached to the objective lens attachment portion 51 having an opening. If the objective lens 70 is directly attached to the objective lens attachment portion 51 while removing the interference optical apparatus 2 from the interference observation apparatus 1, this configuration may be used as a normal microscope apparatus. That is, the interference observation apparatus 1 may be configured by attaching the interference optical apparatus 2 to a normal microscope apparatus.

By the housing 10 of the interference optical apparatus 2, the first attachment portion 11, the second attachment portion 12, the light source 13, the photodetector 14, the first beam splitter 15, the second lens 16, the second beam splitter 17, the reference mirror 21, the first lens 22, the drive element 23, and the stages 24 and 25 are held. Among them, the photodetector 14 and the drive element 23 are electrically coupled to the control unit 31. By the microscope housing 50, the objective lens attachment portion 51, the sample holding table 52, the stages 53 and 54, the tube lens 55, the imaging unit 56, and the eyepiece lens 57 are held. The first attachment portion 11 of the interference optical apparatus 2 includes an opening to be optically coupled to an opening of the objective lens attachment portion 51 of the microscope apparatus. The second attachment portion 12 of the interference optical apparatus 2 includes an opening to be optically coupled to the objective lens 70.

The light source 13 outputs the light. The light source 13 may be a laser light source which outputs coherent laser light, or may be a light source which outputs incoherent light. The light source 13 may be a lamp light source such as a halogen lamp, or an ASE (Amplified spontaneous emission) light source, and preferably a compact light source such as a laser diode, an LED (Light emitting diode) light source, or an SLD (Super luminescent diode) light source.

The photodetector 14 receives the light and outputs a detection signal. The photodetector 14 may be a photomultiplier tube, a line sensor (linear sensor), a CCD area image sensor, or a CMOS area image sensor, and preferably a compact photodetector such as a photodiode or an avalanche photodiode.

The beam splitter 15 is optically coupled to the light source 13 and the photodetector 14, inputs the light output from the light source 13 and outputs the light to the lens 16 along a predetermined direction, and inputs the light arrived from the lens 16 along the predetermined direction and outputs the light to the photodetector 14. The beam splitter 15 include a surface 15a through which the light output from the light source 13 is input, a surface 15b through which light output from the light source 13 is output to the lens 16 and combined light described below is input, a surface 15c through which the input combined light is output to the photodetector 14, and a surface 15d on which part of the light input from the respective surfaces is reflected and through which part of the light is transmitted. The beam splitter 15 is, for example, a half mirror.

The lens 16 is provided on the optical path between the beam splitter 15 and the beam splitter 17, and collimates the light output from the beam splitter 15. In a state where the first attachment portion 11 is optically coupled to the objective lens attachment portion 51, and the objective lens 70 is optically coupled to the second attachment portion 12, when focus is adjusted such that the imaging plane of the imaging unit 56 and the observation object are optically conjugate to each other, the lens 16 is disposed at a position where the position of the photodetector 14 is optically conjugate to both the imaging plane of the imaging unit 56 and the observation object.

The beam splitter 17 is optically coupled to the beam splitter 15, and forms the optical system of the Michelson interferometer. The beam splitter 17 splits the light arrived from the beam splitter 15 through the lens 16 into first split light and second split light. The beam splitter 17 irradiates the observation object with the first split light through the opening of the second attachment portion 12 and the objective lens 70, and inputs the first split light reflected by the observation object. The beam splitter 17 inputs the second split light returning through a reference optical path in which the reference mirror 21 and the lens 22 are included. Then, the beam splitter 17 combines the first split light and the second split light thus input, and outputs the combined light to the opening of the first attachment portion 11 and the beam splitter 15. The beam splitter 17 includes a surface 17a which inputs the light output from the beam splitter 15 and outputs the combined light to the beam splitter 15, a surface 17b which outputs the first split light to the objective lens 70 and inputs the first split light returning from the objective lens 70, a surface 17c which outputs the second split light to the reference optical path and inputs the second split light returning from the reference optical path, a surface 17d which splits the light output from the beam splitter 15 into the first split light and the second split light and combines the first split light returning from the objective lens 70 and the second split light returning from the reference optical path, and a surface 17e which outputs the combined light to the opening of the first attachment portion 11. The beam splitter 17 is, for example, a half mirror.

A reference optical system 20 includes the reference mirror 21, the lens 22, the drive element 23, and the stages 24 and 25. The reference optical system 20 is optically coupled to the beam splitter 17, and disposed on the reference optical path. The lens 22 is optically coupled to the beam splitter 17, and condenses the second split light output from the beam splitter 17 to the reference mirror 21. Further, the lens 22 outputs the second split light reflected by the reference mirror 21 to the beam splitter 17. The drive element 23 is a mirror moving unit which moves the reference mirror 21 in a direction parallel to an optical axis of the lens 22 (a direction of an optical axis of the lens 22). The drive element 23 is, for example, an actuator such as a piezo element or a stepping motor. The stage 24 moves the lens 22 in a direction parallel to the optical axis of the lens 22. The stage 25 integrally moves the reference mirror 21 and the lens 22 in a direction parallel to the optical axis of the lens 22. A distance between the reference mirror 21 and the lens 22 is roughly adjusted by the stage 24, and finely adjusted by the drive element 23. A distance between the reference mirror 21 and the beam splitter 17 is roughly adjusted by the stage 25, and finely adjusted by the drive element 23.

The control unit (controller) 31 is a computer which includes a processor and a memory. The computer may be a personal computer or a smart device such as a tablet terminal. Further, the control unit 31 may include an input unit (keyboard, mouse, tablet terminal, etc.) which receives an input from a user, and a display unit (display, tablet terminal, speaker, vibrator, etc.) which displays an interference intensity, etc. Further, in a case where the display unit can display a screen such as the display or the tablet terminal, the interference image etc. acquired by the imaging unit 56 may be displayed with the interference intensity.

The control unit 31 inputs the detection signal output from the photodetector 14, obtains a phase difference in accordance with an optical path difference between the first split light and the second split light from the splitting to the combining in the beam splitter 17 on the basis of the detection signal, by the processor, and drives the drive element 23 on the basis of the obtained phase difference to control the optical path difference. The control will be described below in detail.

The objective lens 70 is optically coupled to the opening of the second attachment portion 12 of the interference optical apparatus 2, and optically coupled to the beam splitter 17 through the opening. The objective lens 70 condenses the first split light output from the beam splitter 17 to the observation object which is held on the sample holding table 52. Further, the objective lens 70 inputs the first split light reflected by the observation object and outputs the first split light to the beam splitter 17. The stage 53 translates the sample holding table 52 in a direction parallel to an optical axis of the objective lens 70. The stage 54 translates the sample holding table 52 in two directions intersecting with the optical axis of the objective lens 70 (for example, two directions perpendicular to the optical axis of the objective lens 70).

The tube lens 55 is optically coupled to the opening of the objective lens attachment portion 51, and optically coupled to the first attachment portion 11 of the interference optical apparatus 2 through the opening, and further optically coupled to the beam splitter 17 through the first attachment portion. The tube lens 55 outputs the combined light output from the beam splitter 17 through a splitting optical element 60 to the imaging unit 56 and the eyepiece lens 57. The splitting optical element 60 is, for example, a prism. The imaging unit 56 and the eyepiece lens 57 are optically coupled to the tube lens 55 through the splitting optical element 60. The imaging unit 56 receives the combined light output from the tube lens 55 to acquire the interference image. The imaging unit 56 is, for example, an image sensor such as a CCD area image sensor or a CMOS area image sensor. Further, the interference image can be viewed through the eyepiece lens 57.

In the optical system on the sample side (the optical system of the first split light) and the optical system on the reference side (the optical system of the second split light), respectively, the lenses 70 and 22 are provided to form light images at reflection positions (the observation object, the reference mirror 21). In this way, the interference optical system in which the objective lens (or equivalent lens) is provided in both of optical systems is known as a Linnik-type interferometer. In the configuration illustrated in FIG. 1, an aspherical achromatic lens 22 reduced in size and in weight is used in place of the objective lens to achieve the reduction in weight of the optical system on the reference side (the optical system of the second split light).

The stage 53 is configured to move the sample holding table 52 in a direction of the optical axis of the objective lens 70, and can adjust the optical path length of the optical system on the sample side (the optical system of the first split light). The drive element 23 is configured to move the reference mirror 21 in a direction of the optical axis of the lens 22, and can adjust the optical path length of the optical system on the reference side (the optical system of the second split light). The stage 53 and the drive element 23 can adjust a difference between the optical path length of the optical system on the sample side (the optical system of the first split light) and the optical path length of the optical system on the sample side (the optical system of the first split light), and operates as an optical path difference adjusting unit which adjusts the optical path difference between the first split light and the second split light from the splitting to the combining in the interference optical system.

The interference observation apparatus 1 operates as follows. After the light output from the light source 13 transmits the beam splitter 15 and is collimated by the lens 16, the light is split by the beam splitter 17 into the first split light and the second split light. The first split light is condensed through the opening of the second attachment portion 12 by the objective lens 70 to the observation object which is held on the sample holding table 52, and reflected on the surface or the inner portion of the observation object. The reflected first split light is input to the beam splitter 17 through the objective lens 70 and the opening of the second attachment portion 12. The first split light is optically delayed when being reflected by the observation object. The second split light is condensed by the lens 22 to the reference mirror 21, and reflected by the reference mirror 21. The reflected second split light is input to the beam splitter 17 through the lens 22.

The first split light input from the objective lens 70 to the beam splitter 17 and the second split light input from the lens 22 to the beam splitter 17 are combined by the beam splitter 17. The combined light is received by the imaging unit 56 through the opening of the first attachment portion 11, the opening of the objective lens attachment portion 51, and the tube lens 55, and received by the photodetector 14 through the lens 16 and the beam splitter 15. The interference image is acquired by the imaging unit 56 which receives the combined light. Further, the detection signal is output from the photodetector 14 which receives the combined light. Then, the optical path length difference between the first split light and the second split light from the splitting to the combining in the interference optical system is controlled by the control unit 31 on the basis of the detection signal output from the photodetector 14.

The interference observation apparatus 1 can be configured as in modifications illustrated in FIG. 2 to FIG. 5. Further, the configuration in the housing 10 of the interference optical apparatus 2 in the modifications in FIG. 2 to FIG. 4 may be configured in the same way.

Figure 2:
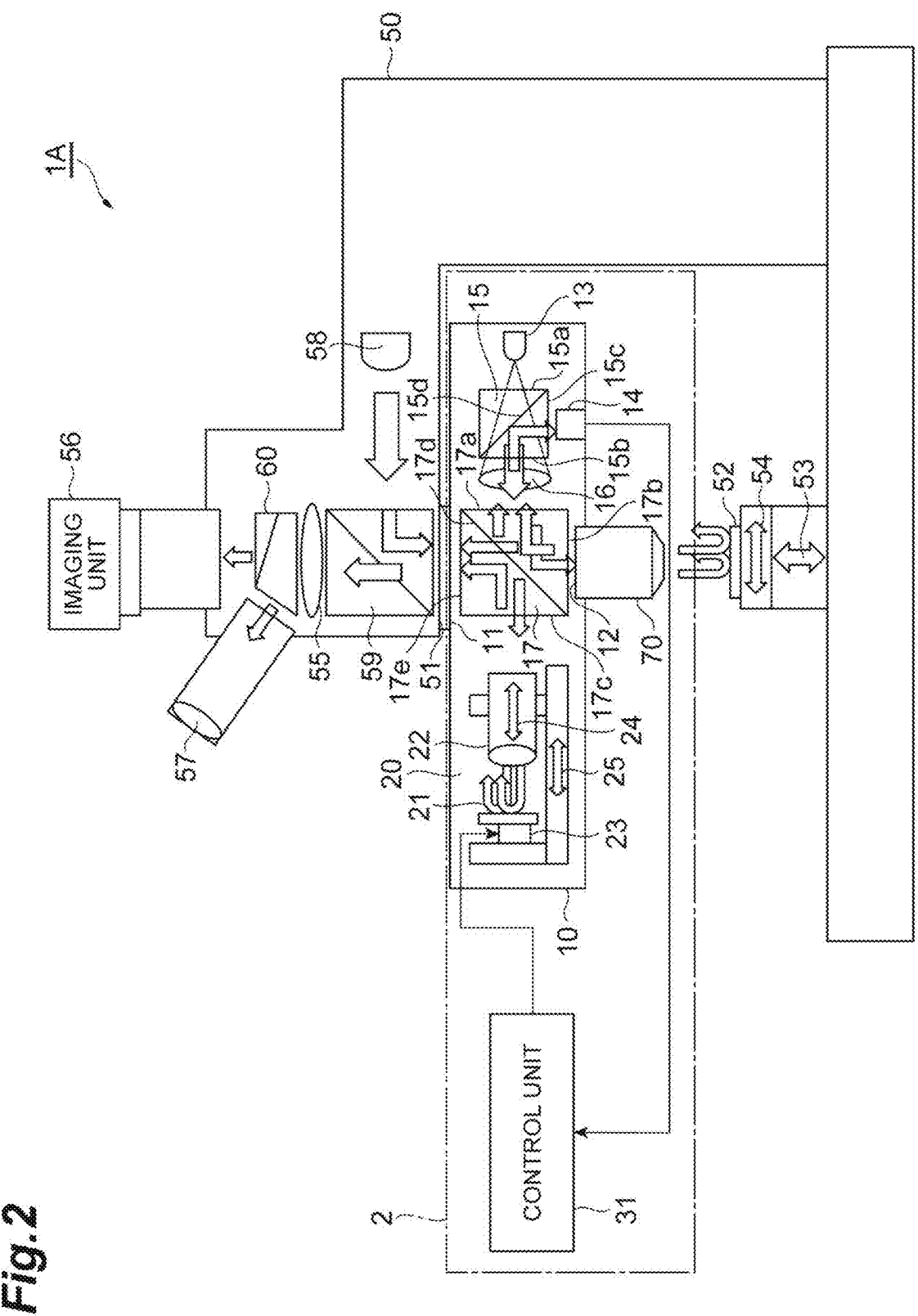
FIG. 2 is a diagram illustrating a configuration of an interference observation apparatus 1A.

An interference observation apparatus 1A of the modification illustrated in FIG. 2 is different from the configuration illustrated in FIG. 1 in that there are used an illumination light source 58 and a beam splitter 59 which are provided in the microscope housing 50. The light output from the illumination light source 58 is reflected by the beam splitter 59, passes through the opening of the objective lens attachment portion 51 and the opening of the first attachment portion 11 of the interference optical apparatus 2, and is split by the beam splitter 17 into the first split light and the second split light. The first split light from the illumination light source 58 returns to the beam splitter 17 through the optical system on the sample side similarly to the first split light from the light source 13. The second split light from the illumination light source 58 returns to the beam splitter 17 through the optical system on the reference side similarly to the second split light from the light source 13. The first split light and the second split light are combined by the beam splitter 17. The combined light is received by the imaging unit 56 through the opening of the first attachment portion 11, the opening of the objective lens attachment portion 51, the beam splitter 59, and the tube lens 55.

In the modification illustrated in FIG. 2, the illumination light source 58 and the imaging unit 56 provided in the microscope housing 50 are used to acquire the interference image. The light source 13 and the photodetector 14 of the interference optical apparatus 2 are used in the control of the optical path difference between the first split light and the second split light from the splitting to the combining in the interference optical system. For example, preferably, the illumination light source 58 provided in the microscope housing 50 is a halogen lamp which outputs visible light, and the imaging unit 56 is a silicon CCD camera which has a sensitivity to the visible band. Further, the light source 13 of the interference optical apparatus 2 is a laser diode which outputs near infrared light, and the photodetector 14 is a photodiode which has a sensitivity to the near infrared band. With this configuration, the imaging unit 56 and the photodetector 14 are not overlapped to each other in the sensitivity band, so that the acquisition of the interference image and the control of the optical path difference can be performed without any influence on each other.

Figure 3:
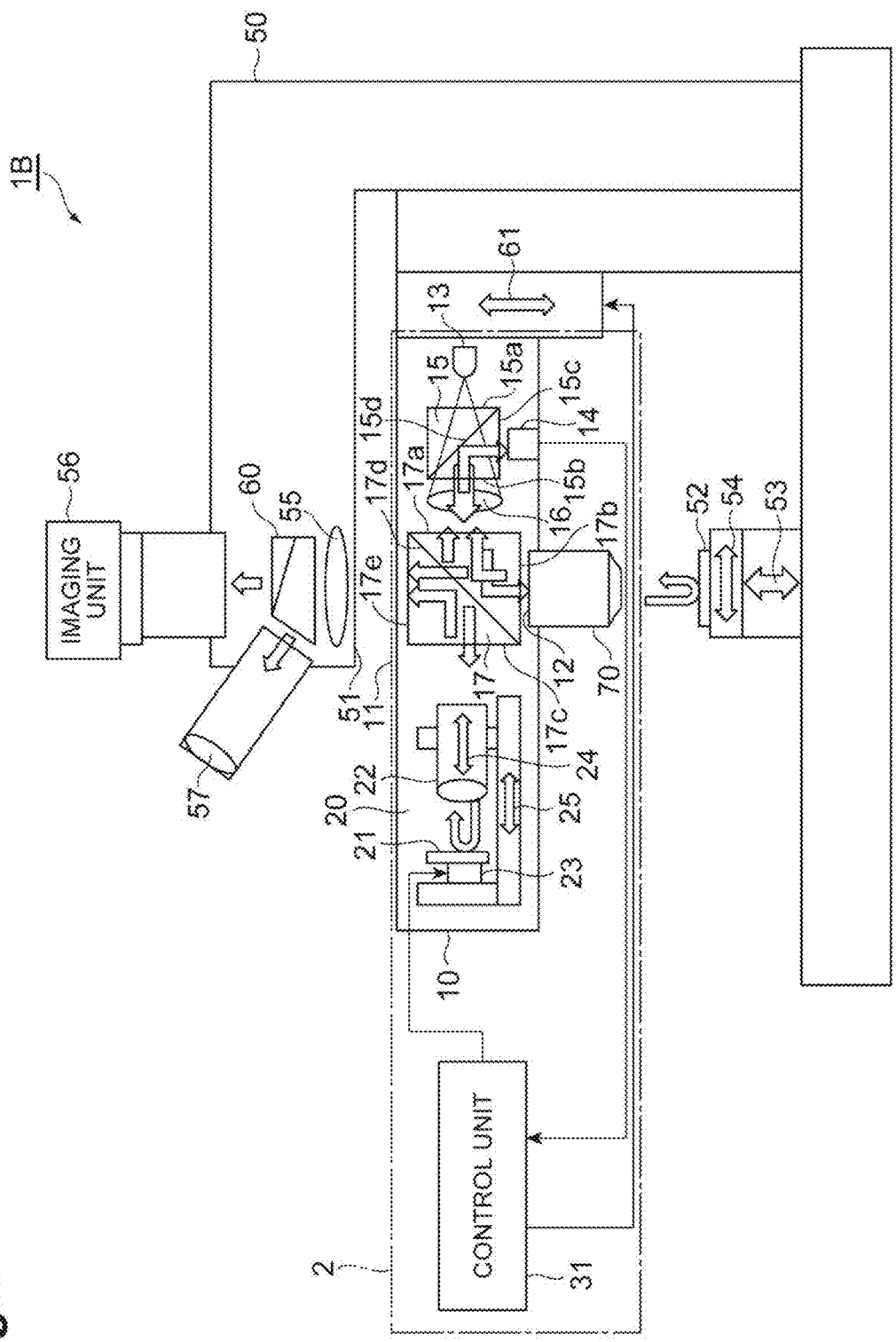
FIG. 3 is a diagram illustrating a configuration of an interference observation apparatus 1B.

An interference observation apparatus 1B of the modification illustrated in FIG. 3 is different from the configuration illustrated in FIG. 1 in that a stage 61 is provided in the microscope housing 50, and the housing 10 of the interference optical apparatus 2 and optical components held by the housing are movable in the direction of the optical axis of the objective lens 70 by the stage 61. The control unit 31 drives the stage 61 to adjust a distance between the housing 10 and the observation object so as to control the focus to the observation object. The stage 61 operates also as the optical path difference adjusting unit which adjusts the optical path difference between the first split light and the second split light from the splitting to the combining in the interference optical system.

Figure 4:
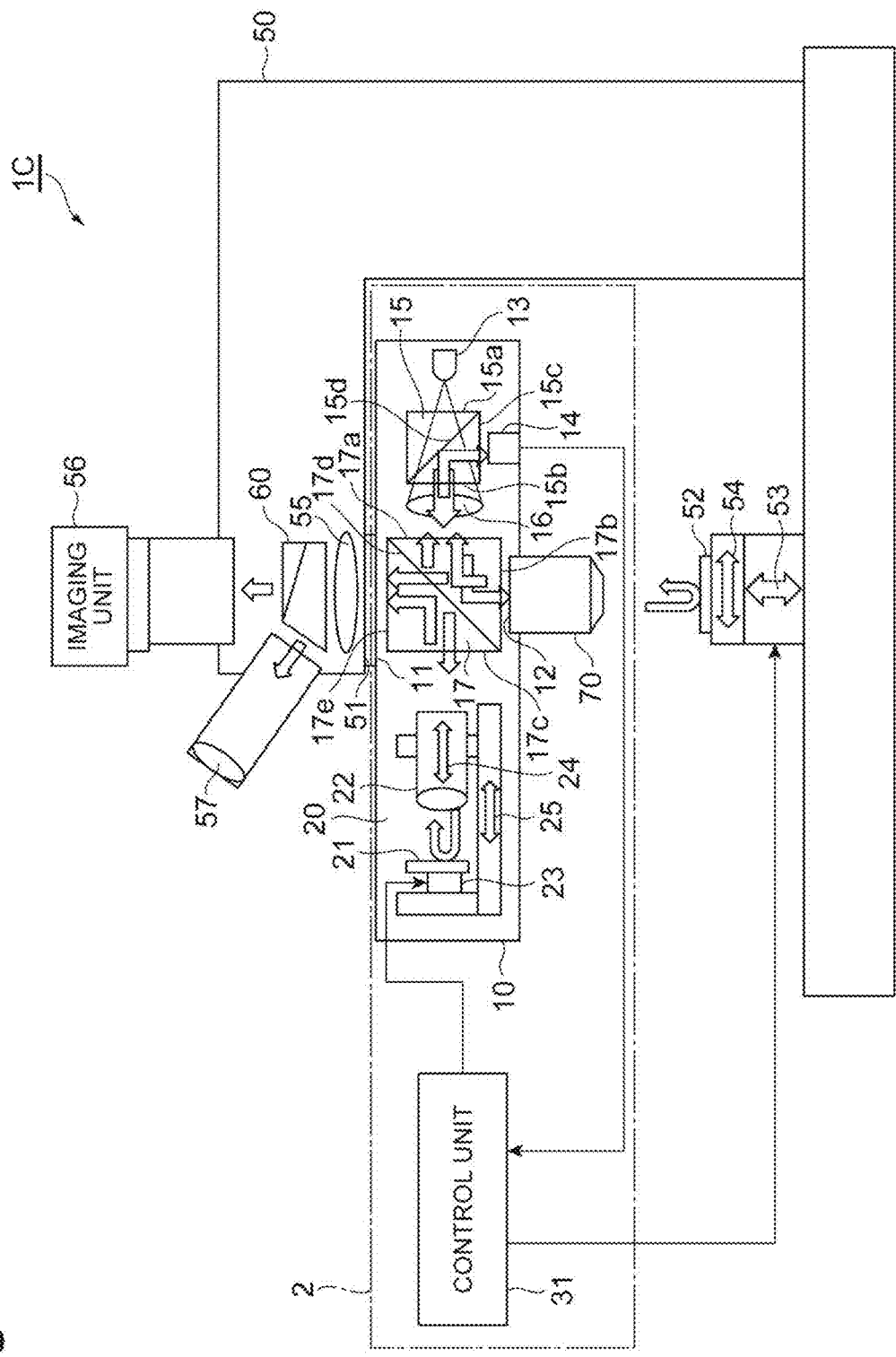
FIG. 4 is a diagram illustrating a configuration of an interference observation apparatus 1C.

An interference observation apparatus 1C of the modification illustrated in FIG. 4 is different from the configuration illustrated in FIG. 1 in that the observation object on the sample holding table 52 is movable in the direction of the optical axis of the objective lens 70 by the stage 53. The control unit 31 drives the stage 53 to adjust the distance between the housing 10 and the observation object so as to control the focus to the observation object. The stage 53 operates also as the optical path difference adjusting unit which adjusts the optical path difference between the first split light and the second split light from the splitting to the combining in the interference optical system similarly to the configuration illustrated in FIG. 1.

In the modifications illustrated in FIGS. 3 and 4, the control unit 31 can adjust both the optical path length of the optical system on the sample side (the optical system of the first split light) and the optical path length of the optical system on the reference side (the optical system of the second split light). The control unit 31 can roughly adjust the optical path difference by driving the stage 61 or the stage 53, and can finely adjust the optical path difference by driving the drive element 23. Further, generally, since the moving range of the drive element is smaller than that of the stage, the control unit 31 adjusts the optical path length of the optical system on the sample side by driving the stage 61 or the stage 53, so that the optical path difference can be made to approach the value of 0 by the driving of the drive element 23.

Figure 5:
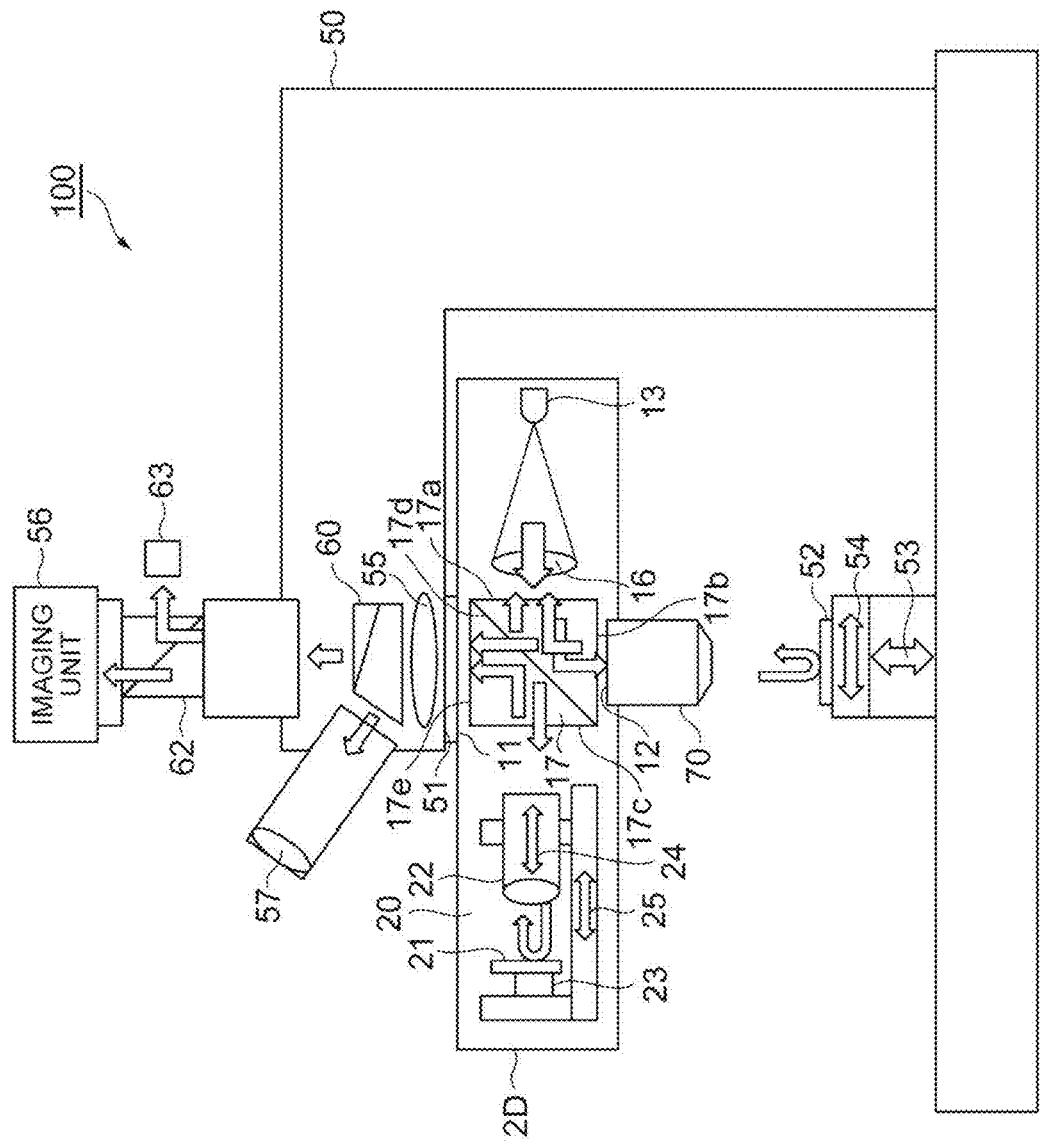
FIG. 5 is a diagram illustrating a configuration of an interference observation apparatus 100 of a comparative example.

An interference observation apparatus 100 of a comparative example illustrated in FIG. 5 is an interference observation apparatus in which a beam splitter 62 and a photodetector 63 are disposed in a camera port of the existing microscope apparatus, and is different from the configuration illustrated in FIG. 1 in that an interference optical apparatus 2D does not include the photodetector 14 and the first beam splitter 15. In the comparative example, the combined light which is combined and output by the beam splitter 17 is received by the imaging unit 56 and the photodetector 63 through the opening of the first attachment portion 11, the opening of the objective lens attachment portion 51, the tube lens 55, and the beam splitter 62. The interference image is acquired by the imaging unit 56 which receives the combined light. Further, the detection signal is output from the photodetector 63 which receives the combined light. Then, the optical path difference between the first split light and the second split light from the splitting to the combining in the interference optical system is controlled on the basis of the detection signal which is output from the photodetector 63.

However, the comparative example illustrated in FIG. 5 is not preferable in the following points. That is, in the existing microscope apparatus, the distance from the tube lens 55 to the imaging plane of the imaging unit 56 is appropriately designed by a microscope maker, and set to be equal to a focal length of the tube lens 55 in general. Further, the imaging plane of the imaging unit 56 is designed in advance to be conjugate to the image plane at the time when viewed through the eyepiece lens 57. However, in a case where the photodetector 63 is provided on a side of the imaging unit 56, there is a need to insert the beam splitter 62 between the tube lens 55 and the imaging unit 56, and therefore, a focal length of the tube lens 55 and the optical distance between the tube lens 55 and the imaging unit 56 come to be mismatched. Further, in this state, when the focus is adjusted to the observation object by the eyepiece lens 57, the focus is deviated on the imaging plane of the imaging unit 56. For the above reason, the comparative example illustrated in FIG. 5 is not preferable.

In the present embodiment, the light source 13 of the interference optical apparatus 2 may be a coherent light source, or may be an incoherent light source. In a case where the incoherent light source is used as the light source 13, there is a need to perform a phase lock and a phase shift by controlling the optical path difference. This is because, in the case of incoherent light, for example white light, the interference is obtained in a case where the optical path difference is a coherence length $\Delta L_C$ or less. When a center wavelength of the incoherent light is set to $\lambda_0$, and a spectrum width of the incoherent light is set to $\Delta\lambda$, the coherence length $\Delta L_C$ is expressed by the following Formula (1). In the case of an LED, the coherence length $\Delta L_C$ is about 10 μm. In the case of a halogen lamp, the coherence length $\Delta L_C$ is about 1 μm.

[Formula 1]

$$\Delta L_C = 2 \times 0.441 \frac{\lambda_0^2}{\Delta\lambda} \quad (1)$$

In the present embodiment, the control unit 31 controls an optical path difference adjusting operation by the drive element 23 on the basis of the detection signal output from the photodetector 14 which receives the combined light, and performs the phase lock and the phase shift.

Here, strictly speaking, the movement of the reference mirror 21 by the drive element 23 causes an imaging condition in the reference optical system 20 to be different. However, an actual scan distance of the reference mirror 21 is about a half of the wavelength of the light, and for example, in a case where a red LED (610 nm in wavelength) is used as the light source 13, the distance becomes about 305 nm. This movement amount is almost the same as a focal depth of the lens 22 (or the objective lens of an equivalent product) or a significantly short distance. Therefore, even when the reference mirror 21 is moved by the drive element 23, it can be considered that the imaging condition in the optical system on the reference side is substantially kept.

In an actual experimental environment, it is not possible to avoid that the optical path length vibrates about 10 nm per 1 second on an experiment table with vibration countermeasure, and further, it is a common thing that the optical path length is disturbed by 100 nm or more per 1 second on an experiment table without vibration countermeasure. Accordingly, in a high-accuracy interference imaging, it is essential that the optical path difference is locked.

As the phase lock, a technique described below may be used (hereinafter, referred to as "first phase lock technique"). In this phase lock technique, the reference mirror 21 is caused to vibrate at a high speed in a sinusoidal manner with a sufficiently small amplitude compared to the wavelength of the output light of the light source 13, and at this time, the detection signal output from the photodetector 14 is detected in synchronization with one time and two times the vibration frequency of the reference mirror 21, to obtain the phase of the interference light. The control unit 31 performs feedback control to make the obtained phase value approach a target value, so that the optical path difference can be locked.

The control unit 31 inputs the detection signal which is an analog signal from the photodetector 14, and outputs an analog signal for the drive control of the drive element 23. The control unit 31 may perform an analog process internally, or may perform a digital process. In the latter case, for example, the control unit 31 may perform an AD conversion on the input detection signal into a digital signal, process the digital signal, perform a DA conversion on the digital signal obtained by the processing to obtain an analog signal, and output the analog signal. In the processing of the digital signal, a microprocessor or an FPGA (Field Programmable Gate Array) may be used.

When a phase difference $\Delta\phi$ corresponding to the optical path difference is generated, an intensity V of the light received by the photodetector 14 is expressed by the following Formula (2). The light receiving intensity V includes an offset component DC and an amplitude AC which are all unknown. Therefore, there is a need to extract the phase difference $\Delta\phi$ where the DC and the AC are not contained by a certain process.

[Formula 2]

$$V = DC + AC \cdot \sin(\Delta\phi) \quad (2)$$

When the reference mirror 21 is caused to vibrate at a high speed in a sinusoidal manner by the drive element 23 with a sufficiently small amplitude compared to the wavelength of the output light of the light source 13, the intensity V of the light received by the photodetector 14 is expressed as the following Formula (3). α is a modulation degree which is determined according to an amplitude of the vibration of the reference mirror 21. ω is an angular frequency of the vibration. t is a time variable.

[Formula 3]

$$V(t) = DC + AC \cdot \sin(\Delta\phi + \alpha \cdot \sin(\omega t)) \quad (3)$$

When the right side of Formula (3) is expanded in a Fourier series, the following Formula (4) is obtained as an approximation formula. $J_1$ and $J_2$ are Bessel functions of the first kind. The second term in the right side of Formula (4a) vibrates at an amplitude $A_{\omega t}$ and an angular frequency $\omega$. Further, the third term in the right side of Formula (4a) vibrates at an amplitude $A_{2\omega t}$ and an angular frequency $2\omega$. Therefore, the detection signal output from the photodetector 14 is synchronously detected with the angular frequency co to obtain the amplitude $A_{\omega t}$, and the detection signal is synchronously detected with the angular frequency $2\omega$ to obtain the amplitude $A_{2\omega t}$.

[Formula 4]

$$V(t)=DC'+A_{\omega t}\sin(\omega t)+A_{2\omega t}\cos(2\omega t)+ \quad (4a)$$

$$A_{\omega t}=2\cdot AC\cdot J_1(\alpha)\cdot\cos(\Delta\phi) \quad (4b)$$

$$A_{2\omega t}=2\cdot AC\cdot J_2(\alpha)\cdot\sin(\Delta\phi) \quad (4c)$$

A ratio of the amplitude $A_{\omega t}$ and the amplitude $A_{2\omega t}$ is expressed by the following Formula (5). Further, the AC indicates the interference intensity of the combined light, and the interference intensity AC is expressed by the following Formula (6). Since the amplitude of the vibration of the reference mirror 21 is constant, $J_1(\alpha)$ and $J_2(\alpha)$ can be obtained on the basis of the amplitude. The phase difference $\Delta\phi$ in accordance with the optical path difference can be obtained on the basis of Formula (5), and the interference intensity AC can be obtained on the basis of Formula (6). The control unit 31 includes a synchronous detection circuit, an adding circuit, and a multiplying and dividing circuit for performing the above processes.

[Formula 5]

$$\frac{A_{2\omega t}}{A_{\omega t}}=\frac{2\cdot AC\cdot J_2(\alpha)\cdot\sin(\Delta\phi)}{2\cdot AC\cdot J_1(\alpha)\cdot\cos(\Delta\phi)}=\frac{J_2(\alpha)}{J_1(\alpha)}\tan(\Delta\phi) \quad (5)$$

[Formula 6]

$$AC^2=\left(\frac{A_{\omega t}}{2\cdot J_1(\alpha)}\right)^2+\left(\frac{A_{2\omega t}}{2\cdot J_2(\alpha)}\right)^2 \quad (6)$$

The present embodiment performs the phase lock using the incoherent light. Conventionally, the coherence of the incoherent light is low, and thus it has been difficult to use the incoherent light in the phase lock. However, in the present embodiment, it is possible to urge an operator to optimize an interference state in the optical system by obtaining the interference intensity AC of the incoherent light. That is, when the optical path difference in the interferometer is sufficiently large compared to the coherence length of the light, the interference intensity AC approaches zero. When the optical path difference in the interferometer is zero, the interference intensity AC becomes a maximum value. The interference intensity AC is obtained to adjust the optical path difference for increasing the interference intensity AC.

The phase lock technique (hereinafter, referred to as "second phase lock technique") using a "spatial filtering detector" can also be used. In this technique, a line sensor having a plurality of pixels arranged in one-dimensional direction or a plurality of photodetectors arranged in one-dimensional direction is used as the photodetector 14. In the following, the description will be given about a case where four photodetectors arranged at equal intervals are used. An inclination is given to both or any one of the optical system on the measurement side and the optical system on the reference side to make interference fringes appear, and in this state, the inclination of the interference fringes is adjusted to set the light receiving intensities $V_1$ to $V_4$ of the four photodetectors to be obtained as the following Formula (7).

[Formula 7]

$$V_1=DC+AC\cdot\sin(\Delta\phi) \quad (7a)$$

$$V_2=DC+AC\cdot\sin(\Delta\phi+\pi/2)=DC-AC\cdot\cos(\Delta\phi) \quad (7b)$$

$$V_3=DC+AC\cdot\sin(\Delta\phi+\pi)=DC-AC\cdot\sin(\Delta\phi) \quad (7c)$$

$$V_4=DC+AC\cdot\sin(\Delta\phi+3\pi/2)=DC+AC\cdot\cos(\Delta\phi) \quad (7d)$$

For applying an inclination to both or any one of the optical system on the measurement side and the optical system on the reference side, for example, the sample holding table 52 or the reference mirror 21 may be inclined, or any one of the lenses may be inclined, or a wedge-shaped prism having different thicknesses along a predetermined direction may be inserted on the optical path.

$A_1$ and $A_2$ are obtained from the light receiving intensities $V_1$ to $V_4$ by the following Formula (8), and a ratio of $A_1$ and $A_2$ is obtained by the following Formula (9). Further, the interference intensity AC is expressed by the following Formula (10). From these Formulas, the phase difference $\Delta\phi$ in accordance with the optical path difference can be obtained, and the interference intensity AC can also be obtained. The control unit 31 may realize the above processes by a simple electric circuit.

[Formula 8]

$$A_1=V_1-V_3=2\cdot AC\cdot\sin(\Delta\phi) \quad (8a)$$

$$A_2=V_4-V_2=2\cdot AC\cdot\cos(\Delta\phi) \quad (8b)$$

[Formula 9]

$$\frac{A_1}{A_2}=\frac{2\cdot AC\cdot\sin(\Delta\phi)}{2\cdot AC\cdot\cos(\Delta\phi)}=\tan(\Delta\phi) \quad (9)$$

$$AC^2=\left(\frac{A_1}{2}\right)^2+\left(\frac{A_2}{2}\right)^2 \quad (10)$$

In this way, the control unit 31 obtains the phase difference in accordance with the optical path difference and also obtains the interference intensity, controls the optical path difference adjusting operation by the drive element 23, so that the optical path difference is made small on the basis of the obtained interference intensity, and the optical path difference is kept constant on the basis of the obtained phase difference. Further, when the optical path difference is adjusted, any one of the stage 53 and the drive element 23 may be controlled, however, the optical path difference can be roughly adjusted by the control of the stage 53, and the optical path difference can be finely adjusted by the control of the drive element 23.

Figure 7:
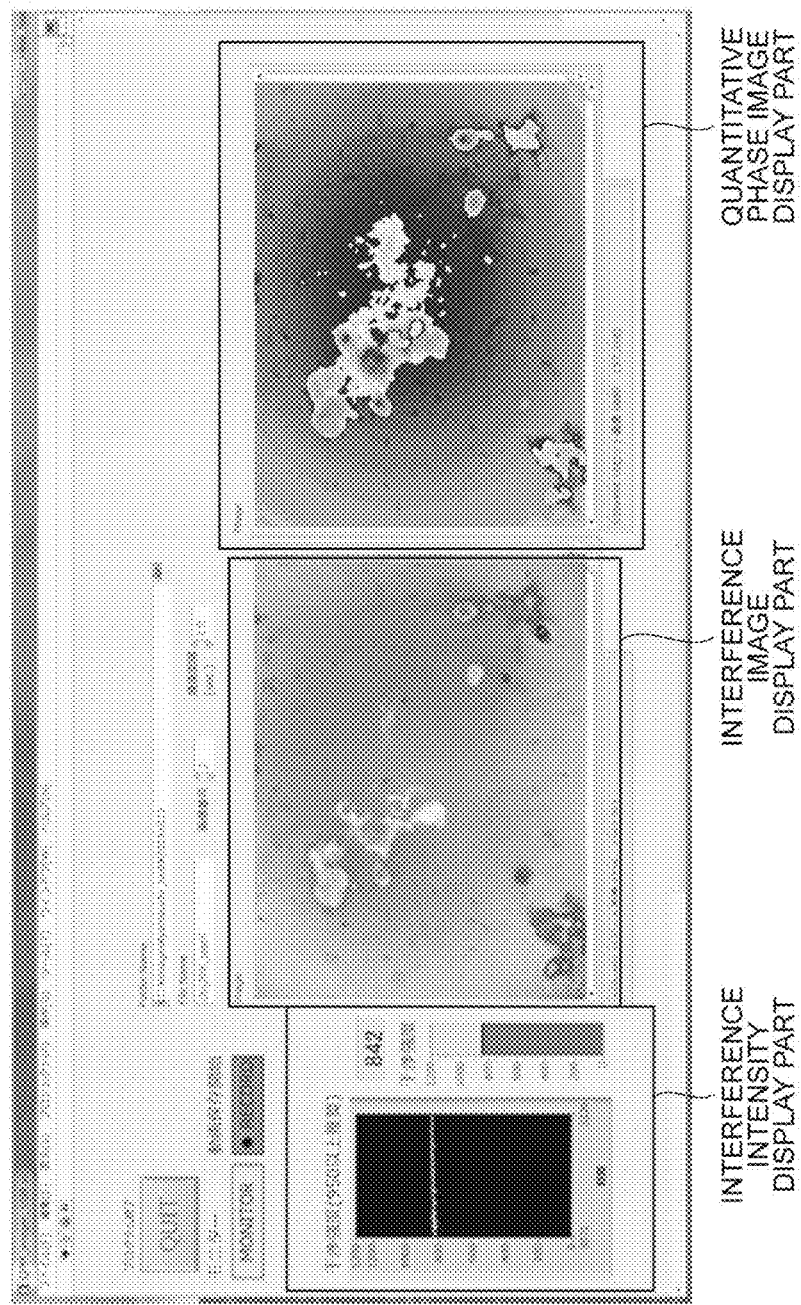
FIG. 7 is a diagram illustrating an example of information which is displayed on a display unit (display).

When the optical path difference is made small on the basis of the obtained interference intensity, the stage 53 may be automatically moved. Further, the interference intensity may be notified to the user to move the stage 53 by the user's operation. For example, the interference intensity is displayed on the display unit of the control unit 31, or a display unit separately provided from this unit so as to notify the interference intensity to the user. The display unit may be a visual unit such as a display, an LED bar, an analog panel meter, or a digital panel meter, or an auditory unit such as a buzzer or a speaker which outputs a sound having a magnitude in accordance with the interference intensity, or further a tactile unit such as a vibrator which gives vibrations having a magnitude in accordance with the interference intensity to the user. The user moves the stage 53 in a direction of the optical axis of the objective lens 70 in order to increase the interference intensity which is displayed on the display unit. FIG. 7 is a diagram illustrating an example of information displayed on the display unit (display). In this example, the interference intensity is simultaneously displayed in three modes of a numerical value, a bar, and a graph showing temporal variation. Further, in this example, the interference image and a phase image (to be described below) are also displayed.

When the interference intensity is increased, it is preferable that the optical path difference is minimized. However, even in a case where the focus or the optical axis of the imaging system of any one of the optical system on the sample side and the optical system on the reference side is deviated, the interference intensity is reduced. Therefore, the first thing to do for increasing the interference intensity is to adjust the optical path difference to be reduced, and further, to adjust the focus and the optical axis of each imaging system of the optical system on the sample side and the optical system on the reference side. For example, the lens 22 may be moved in the direction of the optical axis by the stage 24 in order to increase the interference intensity. In this case, the focal position of the lens 22 can be optimally adjusted with respect to the reference mirror 21, and the interference intensity can be increased.

As an algorithm for maximizing the interference intensity, it is considered a method in which one of adjustment mechanisms (the optical path difference, the focus, and the optical axis) is moved in one direction while recording the interference intensity, the adjustment mechanism is moved in the reverse direction when the interference intensity passes by an optimal position and begins to be lowered, and a point at which the interference intensity is obtained within several % of error in maximum intensity obtained during scanning in one direction is considered as an optimal value. In a case where there are a plurality of adjustment points, an algorithm is considered in which the searching of such an optimal value is performed sequentially on each of the adjustment points, the adjustment is performed once more or in plural times as needed after one cycle of adjustment so as to realize an optimal state of the optical system as a whole.

Figure 13:
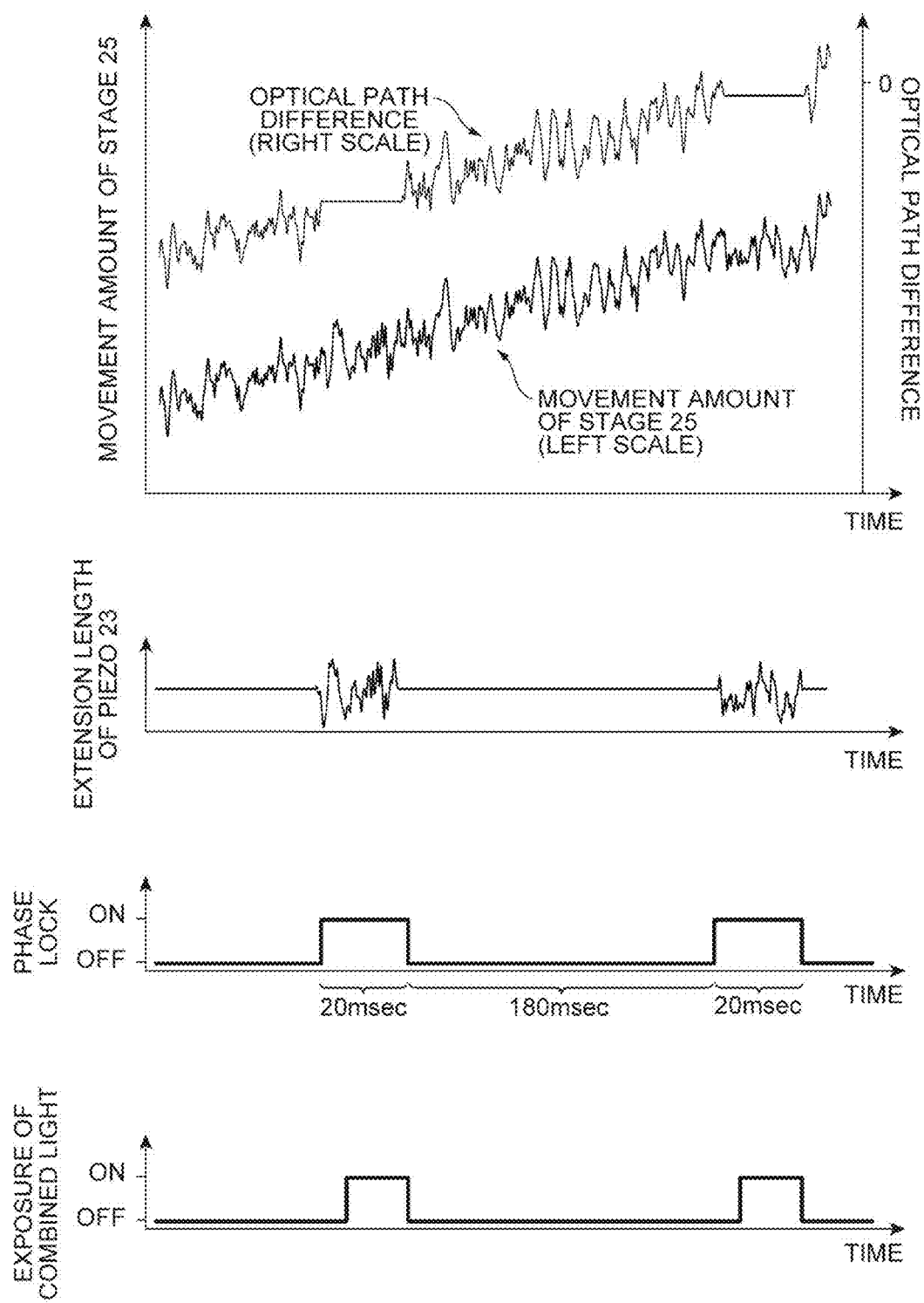
FIG. 13 is a diagram for describing a method of maximizing an interference intensity.

Further, as a method of maximizing the interference intensity, one or some of the adjustment mechanisms (the optical path difference, the focus, and the optical axis) may be moved while applying the phase lock intermittently. For example, in a case where the interference intensity is maximized while moving the stage 25 by the user's operation, an actual movement amount causes the vibration due to a mechanical factor of the optical system including the stage 25. Therefore, as illustrated in FIG. 13, when the interference optical system is adjusted while repeatedly turning ON and OFF the phase lock, the optical path difference is intermittently stabilized. FIG. 13 is a diagram for describing a method of maximizing the interference intensity. In this drawing, there are illustrated the temporal variations of the movement amount of the stage 25, the optical path difference, an extension length of the piezo element 23, turning ON/OFF of the phase lock, and turning ON/OFF of the exposure of the combined light.

In a case where the interference optical system is adjusted while intermittently performing the phase lock as described above, the turning ON/OFF of the exposure of the combined light by the imaging unit 56 may be performed in accordance with the turning ON/OFF of the phase lock. In this case, the imaging unit 56 is controlled such that an exposure period of the imaging unit 56 falls within the ON period of the phase lock. For example, the control unit 31 controls the imaging by the imaging unit 56 such that the exposure period of the imaging unit 56 falls within the ON period of the phase lock. For this reason, the user can confirm the interference image in which the phase lock is in the ON state periodically while adjusting the interference optical system, and therefore, the interference image can be confirmed without being affected with a mechanical factor.

In a case where the adjustment mechanism is moved while intermittently performing the phase lock and the interference image at timing when the phase lock is being applied is displayed, a target phase difference in each intermittent phase lock is preferably set to the same value at every cycle. In this case, the optical path difference L in the ON period of each phase lock is stabilized to $L = \Delta L + N\lambda$ (N is an integer, $\lambda$ is the center wavelength of the light source, and $\Delta L$ is an offset optical path difference corresponding to the phase difference). Therefore, a relative phase difference is constant at an imaging timing of each interference image even while the optical path difference is being adjusted. With this configuration, a pattern of the interference fringes is almost the same, and images only different in contrast can be sequentially acquired. Since information necessary for the purpose of maximizing the interference intensity is not the phase of the interference fringes but the contrast of the interference fringes, moving the adjustment mechanism while observing the interference image only different in contrast has less burden on an operator's work compared to moving the adjustment mechanism in a state where the interference fringes are changing.

In this way, the contrast of the interference fringes is useful as secondary information of the interference intensity. Further, shaking of the optical path difference additionally occurs even in the adjustment of the focus and the optical axis which are not directly related to the optical path difference. The method of moving the adjustment mechanism while intermittently performing the phase lock is effective even in the adjustment of the focus and the optical axis.

There is a need to appropriately set a ratio of the ON period of the phase lock and the OFF period of the phase lock and a cycle of repeating ON and OFF of the phase lock. First, when the ON period of the phase lock is too short, it is insufficient for stabilizing the phase lock, and an exposure time is short when the imaging unit 56 performs the exposure. Therefore, since the phase lock mechanism can be stabilized in the Optical path length in a transition time (depending on a mechanical factor of the optical system) of about 1 msec to 5 msec, it is preferable that the ON period of the phase lock be longer than at least 1 msec. Here, in a case where a sample (for example, glass surface) having a low reflectance is observed, it is preferable to take a time width for enabling to capture an image of the interference fringes with a sufficient light amount, and it is preferable to set the time width to at least 20 msec or longer from the viewpoint of the exposure period of the imaging unit 56.

On the other hand, there may be a problem even when the ON period of the phase lock is too long. The cycle of repeating ON and OFF of the phase lock cannot be set to be smaller than the reciprocal of the ON period of the phase lock. For example, when the ON period of the phase lock is 5 seconds, it is a matter of course that the cycle repeating ON and OFF of the phase lock also has to be longer than 5 seconds. In this case, since the cycle of displaying the interference image becomes longer than 5 seconds, operability of the operator is degraded. Further, in a case where the ON period of the phase lock is long, there also occurs a problem related to the extension range of the piezo element 23. An extension distance of the piezo element 23 is adjusted by the feedback control in order to remove a change in the optical path length caused by the movement of the adjustment mechanism (the optical path difference, the focus, and the optical axis) during the phase lock is turned ON, however, the extension range of the piezo element 23 to be used in the feedback control is about ±8 μm at most, and in a case where the change in the optical path length caused by the movement of the adjustment mechanism (the optical path difference, the focus, and the optical axis) exceeds the range, the feedback control does not work. For these reasons, the ON period of the phase lock is preferably 3 seconds or less for example.

Further, since the cycle of repeating ON and OFF of the phase lock becomes the same as the cycle of displaying the interference image, for operability of the operator being not degraded, the cycle is preferably set to be less than 3 seconds. In a case where the ON period of the phase lock and the cycle of repeating ON and OFF of the phase lock are preferably set, the time width of the OFF period of the phase lock is also obtained automatically.

FIG. 13 illustrates a timing chart in a case where the optical path length is adjusted while the phase lock is intermittently performed, and also illustrates specific numerical values of the length of each period. The ON period of the phase lock is set to 20 msec, and the cycle of repeating ON and OFF of the phase lock is set to 200 msec. In this modification, the interference image can be stably obtained with the interval of 200 msec.

Further, the OFF period of the phase lock may be set to 30 msec or less. Since the interference image is not acquired in the OFF period of the phase lock, the interference image is not smoothly changed for the operator when the OFF period of the phase lock is larger than 30 msec, and therefore, the observation is not easy. For this reason, the OFF period of the phase lock is set to 30 msec or less to enable smooth change of the interference image for the operator. Further, the OFF period and the ON period of the phase lock are set, and the cycle of repeating ON and OFF of the phase lock may be calculated, and the OFF period of the phase lock and the cycle of repeating ON and OFF of the phase lock are set, and the ON period of the phase lock may be set.

Figure 14:
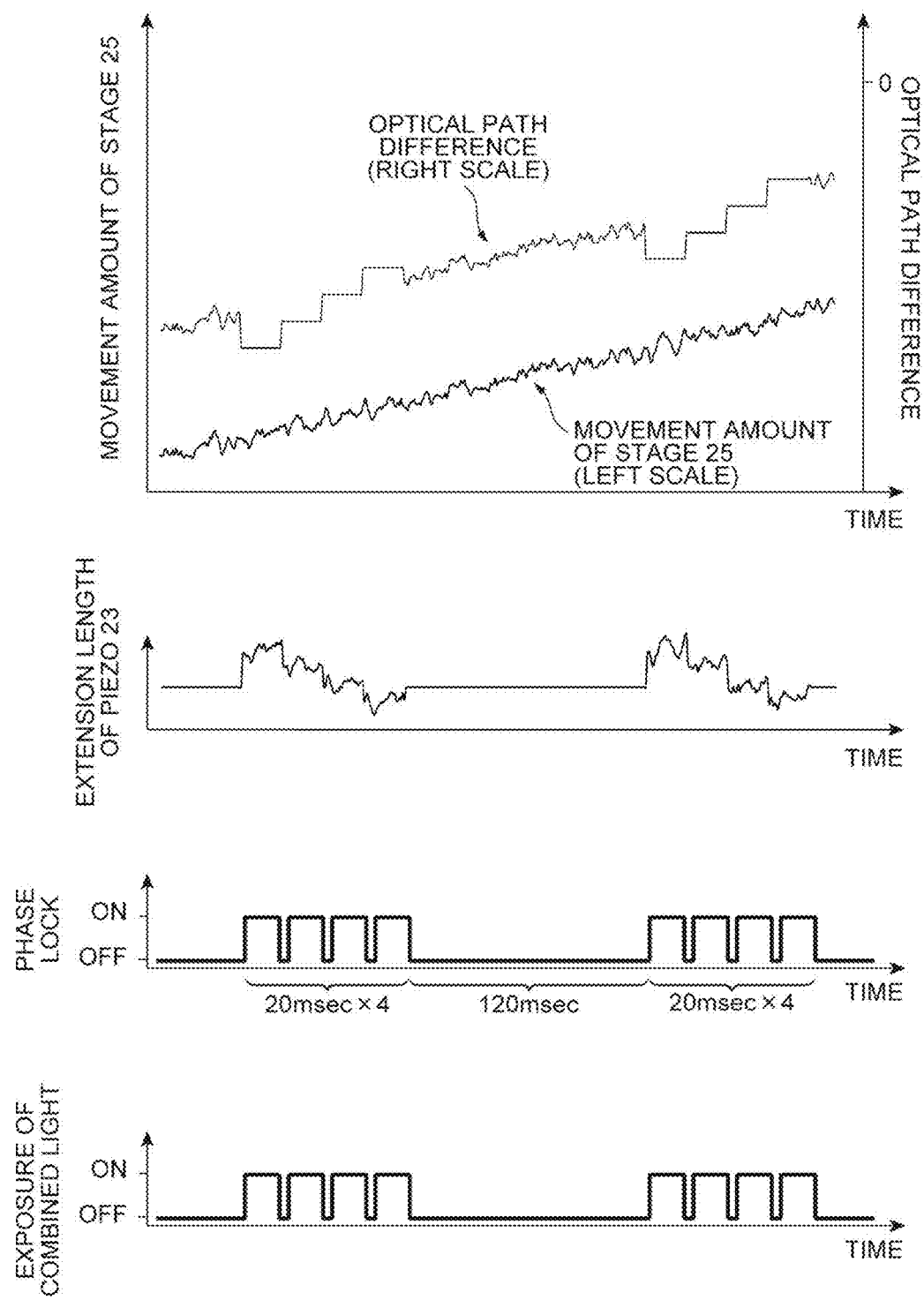
FIG. 14 is a diagram for describing another method of maximizing the interference intensity.

Further, as illustrated in FIG. 14, the phase shift may be performed with the intermittent phase lock. FIG. 14 is a diagram for describing another method of maximizing the interference intensity. The drawing also illustrates the temporal variations of the movement amount of the stage 25, the optical path difference, the extension length of the piezo element 23, turning ON/OFF of the phase lock, and turning ON/OFF of the exposure of the combined light. In the timing chart illustrated in the drawing, the phase shift is performed during a period of each phase lock. Specifically, a plurality (4 times in FIG. 14) of ON periods of the phase lock are intermittently provided while interposing stagnation periods, and the phase shift is performed during a period of each phase lock. Thereafter, the OFF period of the phase lock is provided, a plurality of periods of the phase lock are intermittently provided again while interposing the stagnation periods, and the phase shift is performed during a period of each phase lock again. As a phase shift method, it is preferable to use a well-known λ/4 phase shift method. In the method illustrated in FIG. 14, the optical path difference is adjusted while the phase lock is intermittently performed, so that the interference image and the phase image are obtained at an interval of 200 msec even while adjusting the optical path difference.

Figure 6:
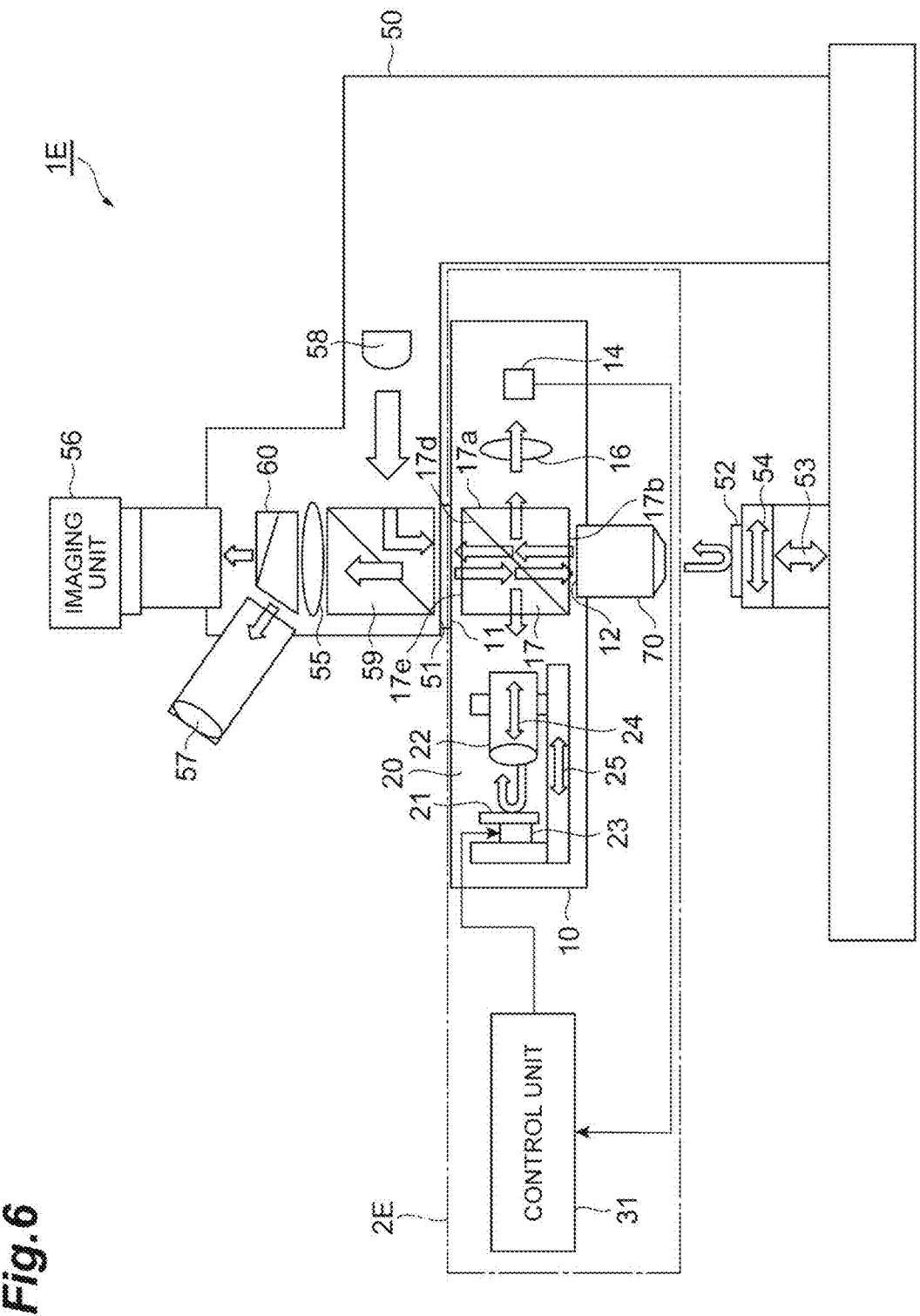
FIG. 6 is a diagram illustrating a configuration of an interference observation apparatus 1F.

Next, another embodiment will be described. FIG. 6 is a diagram illustrating a configuration of an interference observation apparatus 1E of another embodiment. The interference observation apparatus 1E includes an interference optical apparatus 2E, the microscope housing 50, the objective lens attachment portion 51, the sample holding table 52, the stages 53 and 54, the tube lens 55, the imaging unit 56, the eyepiece lens 57, the illumination light source 58, the beam splitter 59, and the objective lens 70. Further, the interference optical apparatus 2E includes the housing 10, the first attachment portion 11, the second attachment portion 12, the photodetector 14, the second lens 16, the second beam splitter 17, the reference mirror 21, the first lens 22, the drive element 23, the stages 24 and 25, and the control unit 31.

Compared to the configuration of the interference observation apparatus 1A illustrated in FIG. 2, the interference observation apparatus 1E illustrated in FIG. 6 is different in that the interference optical apparatus 2E is included in place of the interference optical apparatus 2. Similarly in the interference observation apparatus 1E, in the microscope apparatus which includes the illumination light source 58 and the imaging unit 56 for capturing an image of the light passing through the objective lens 70 attached to the objective lens attachment portion 51 having the opening, the housing 10 of the interference optical apparatus 2E is disposed between the objective lens attachment portion 51 and the objective lens 70.

Compared to the configuration of the interference optical apparatus 2 illustrated in FIG. 2, the interference optical apparatus 2E illustrated in FIG. 6 is different in that the light source 13 and the first beam splitter 15 are not included. In the housing 10 of the interference optical apparatus 2E, the first attachment portion 11, the second attachment portion 12, the photodetector 14, the second lens 16, the second beam splitter 17, the reference mirror 21, the first lens 22, the drive element 23, and the stages 24 and 25 are held. Among them, the photodetector 14 and the drive element 23 are electrically coupled to the control unit 31. The first attachment portion 11 of the interference optical apparatus 2E includes an opening which is optically coupled to the opening of the objective lens attachment portion 51 of the microscope apparatus. The second attachment portion 12 of the interference optical apparatus 2E includes an opening which is optically coupled to the objective lens 70.

The interference observation apparatus 1E operates as follows. The light output from the illumination light source 58 is reflected by the beam splitter 59, passes through the opening of the objective lens attachment portion 51 and the opening of the first attachment portion 11 of the interference optical apparatus 2E, and is split by the beam splitter 17 into the first split light and the second split light. The first split light returns to the beam splitter 17 through the optical system on the sample side. The second split light returns to the beam splitter 17 through the optical system on the reference side. The first split light and the second split light are combined by the beam splitter 17. The combined light is received by the photodetector 14, and received by the imaging unit 56 through the opening of the first attachment portion 11, the opening of the objective lens attachment portion 51, the beam splitter 59, and the tube lens 55. The interference image is acquired by the imaging unit 56 which receives the combined light. Further, the detection signal is output from the photodetector 14 which receives the combined light. Then, the optical path difference between the first split light and the second split light from the splitting to the combining in the interference optical system is controlled by the control unit 31 on the basis of the detection signal output from the photodetector 14.

The interference optical apparatus 2E with such a configuration does not include the light source 13 and the first beam splitter 15, so that it can be made small and inexpensive. In general, the microscope apparatus includes an illumination light source which outputs the incoherent light, so that the interference observation apparatus 1E can be configured at a low cost by attaching the interference optical apparatus 2E.

Next, an example of the interference observation apparatus 1 will be described. The configuration illustrated in FIG. 1 is used. An LED having a wavelength of 610 nm is used as the light source 13. A photodiode is used as the photodetector 14. Further, a camera equipped with the CCD area image sensor is used as the imaging unit 56.

As the observation object, a HeLa cell from a cervical cancer is cultured on a holding substrate formed of a half mirror, and fixed with ethanol. At the time of observation, several drops of the pure water are trickled onto the cell, a cover glass is set thereon, and the cell is observed by the objective lens 70 from the upper side.

A piezo element is used as the drive element 23, and the angular frequency ω of the vibration of the reference mirror 21 by the piezo element is set to 2.3 kHz. The components of 2.3 kHz and 4.6 kHz in the detection signal output from the photodetector 14 are synchronously detected by the control unit 31. The phase difference Δϕ is obtained from the above Formula (5) on the basis of the synchronous detection result, and the center position of the vibration of the reference mirror 21 caused by the drive element 23 is subjected to the feedback control on the basis of the phase difference Δϕ to perform the phase lock and the phase shift.

Figure 8:
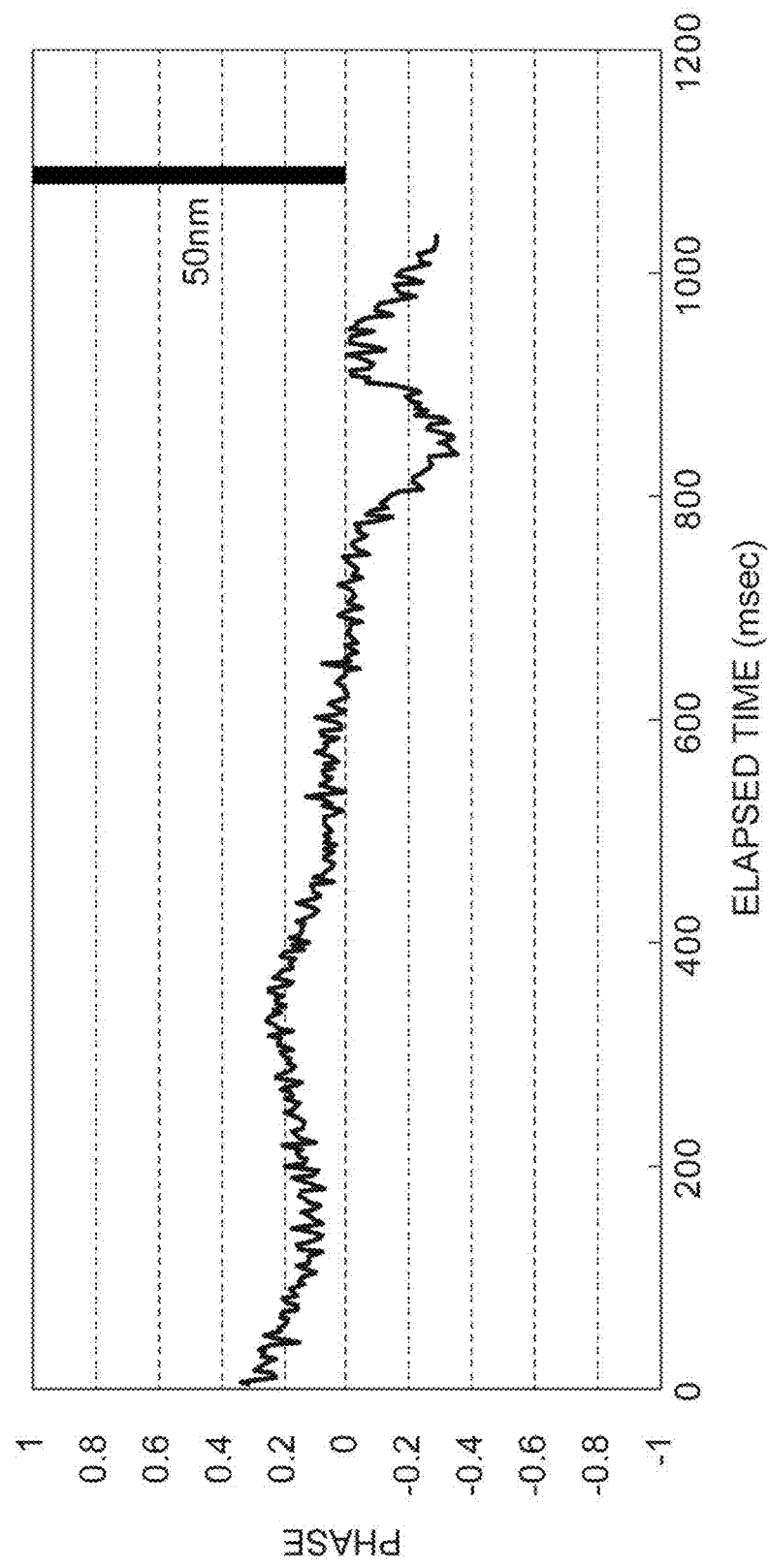
FIG. 8 is a graph illustrating a temporal variation in phase in a case where feedback control is not performed.
Figure 9:
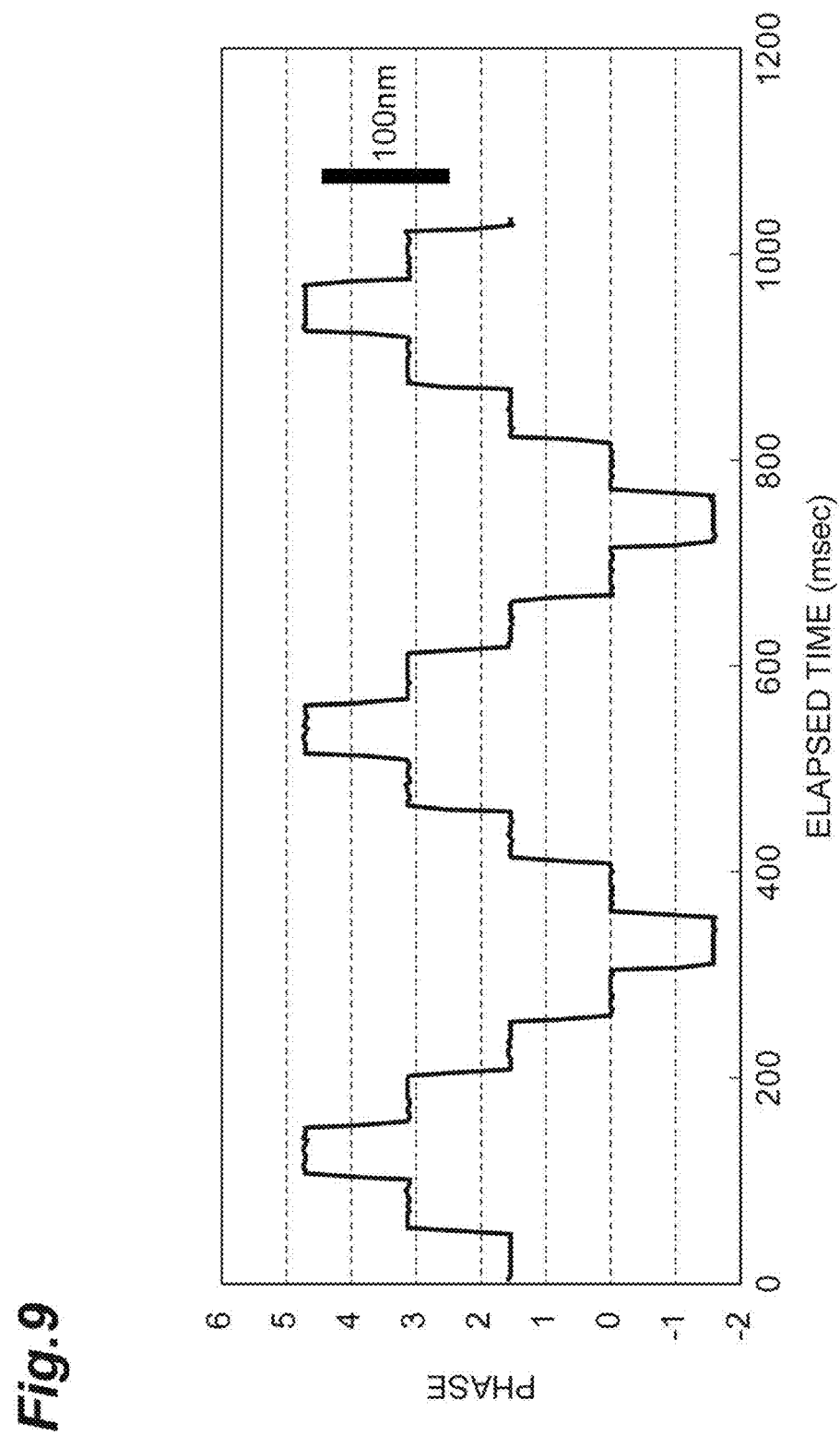
FIG. 9 is a graph illustrating a temporal variation in phase in a case where the feedback control is performed.

FIG. 8 is a graph illustrating a temporal variation of the phase in a case where the feedback control is not performed. FIG. 9 is a graph illustrating the temporal variation of the phase in a case where the feedback control is performed. In a case where the feedback control is not performed (FIG. 8), a drift of the optical path length of about 10 nm per second is recognized. On the other hand, in a case where the feedback control is performed (FIG. 9), the phase shift and the phase lock are exactly realized by π/2.

Figure 12:
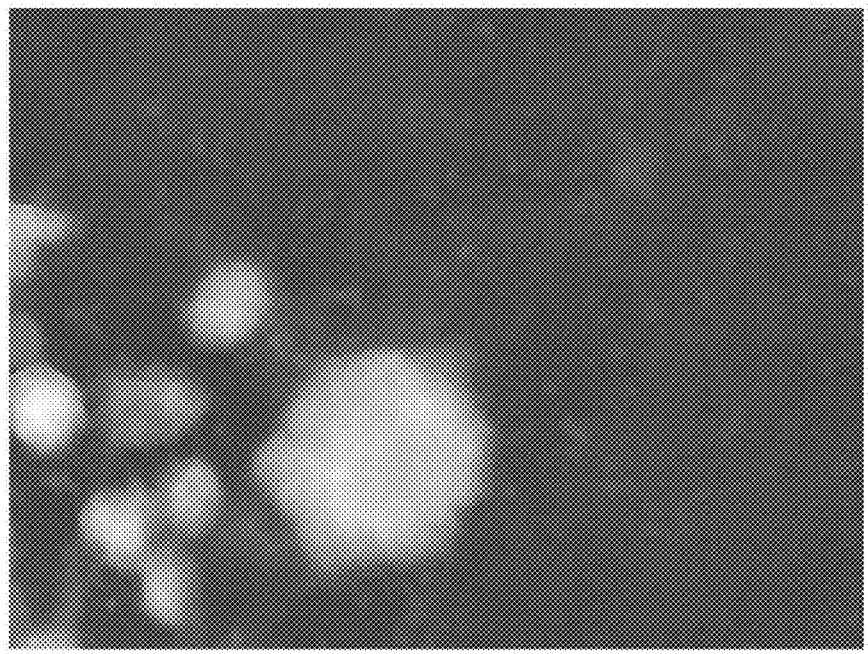
FIG. 12 is a view showing a phase image.

FIG. 10 and FIG. 11 include views showing the interference images acquired by performing the phase shift and the phase lock. An interference image $I_2(x, y)$ shown in (b) in FIG. 10 is different from an interference image $I_1(x, y)$ shown in (a) in FIG. 10 in phase by π/2, an interference image $I_3(x, y)$ shown in (a) in FIG. 11 is different in phase by π, and an interference image $I_4(x, y)$ shown in (b) in FIG. 11 is different in phase by 3π/2. A quantitative phase image $\Psi(x, y)$ is obtained from these interference images $I_1$ to $I_4$ by the following Formula (11). Further, x and y are variables indicating the positions in the respective images. The image $\psi(x, y)$ is subjected to phase unwrapping, and a distortion component of the background is flattened by the calculation of the shading correction using a Zernike polynomial, so that the quantitative phase image shown in FIG. 12 is obtained.

[Formula 11]

$$\psi(x, y) = \tan^{-1}\left(\frac{I_1(x, y) - I_3(x, y)}{I_4(x, y) - I_2(x, y)}\right) \quad (11)$$

Next, the effects of the present embodiment will be described. In the present embodiment, the housing 10 and the optical components held by the housing are integrated in the interference optical apparatus 2, and therefore, the interference observation apparatus 1 including the interference optical apparatus 2 can perform the optical adjustment with ease, so that it is possible to acquire the interference image of the observation object with an inexpensive configuration. In the configurations illustrated in FIGS. 1, 3, and 4, only one light source is provided, and therefore, the configuration can be made at a low cost, and further, the configuration can be easily set up when the apparatus is assembled or readjusted after conveyance.

Further, in a case where the interference image is acquired using the incoherent light, speckles and diffraction noises are suppressed, so that the acquired interference image can have a good image quality. Further, since the phase lock and the phase shift can be made with accuracy, a high-speed sweeping of the optical path difference and a high-speed imaging are not necessary, and the quantitatively excellent interference image can be acquired without irradiating the observation object with high intensity light.

The interference optical apparatus, the interference observation apparatus, and the interference observation method according to one aspect of the present invention are not limited to the above-described embodiments and configuration examples, and various modifications can be made.

The interference optical apparatus according to one aspect of the present invention is an interference optical apparatus to be disposed between an objective lens attachment portion and an objective lens in a microscope apparatus including an imaging unit for capturing an image of light passing through the objective lens attached to the objective lens attachment portion having an opening, and includes (1) a first attachment portion including an opening to be optically coupled to the opening of the objective lens attachment portion; (2) a second attachment portion including an opening to be optically coupled to the objective lens; (3) a light source for outputting light; (4) a photodetector for receiving combined light to output a detection signal; (5) a first beam splitter optically coupled to the light source and the photodetector, for inputting the light output from the light source and outputting the light along a predetermined direction, and inputting the combined light and outputting the combined light to the photodetector; (6) a second beam splitter optically coupled to the first beam splitter, for splitting the light output from the first beam splitter into first split light and second split light, irradiating an observation object with the first split light through the objective lens and inputting the first split light reflected by the observation object, inputting the second split light passing through a reference optical path, combining these input first split light and second split light and outputting the combined light to the opening of the first attachment portion and the first beam splitter; (7) a reference optical system optically coupled to the second beam splitter and provided on the reference optical path, and including a first lens for condensing the second split light output from the second beam splitter, a reference mirror for reflecting the second split light condensed by the first lens to the first lens, and a mirror moving unit for moving the reference mirror in a direction of an optical axis of the first lens; and (8) a housing for holding the first attachment portion, the second attachment portion, the light source, the photodetector, the first beam splitter, the second beam splitter, and the reference optical system.

It is preferable that the interference optical apparatus according to one aspect of the present invention further includes a second lens provided on an optical path between the first beam splitter and the second beam splitter, and, in a state where the first attachment portion is optically coupled to the objective lens attachment portion and the objective lens is optically coupled to the second attachment portion, when focus is adjusted such that an imaging plane of the imaging unit and the observation object are optically conjugate to each other, the second lens is disposed at a position where a position of the photodetector is optically conjugate to both the imaging plane of the imaging unit and the observation object. Further, it is preferable that the light source outputs incoherent light.

It is preferable that, in a case where the microscope apparatus includes an illumination light source, in the interference optical apparatus according to one aspect of the present invention, the second beam splitter is optically coupled to the first beam splitter, optically coupled to the illumination light source through the opening of the objective lens attachment portion and the opening of the first attachment portion, and splits both the light output from the first beam splitter and light output from the illumination light source into first split light and second split light.

The interference optical apparatus according to one aspect of the present invention may be an interference optical apparatus to be disposed between an objective lens attachment portion and an objective lens in a microscope apparatus including an illumination light source and an imaging unit for capturing an image of light passing through the objective lens attached to the objective lens attachment portion having an opening, and include (1) a first attachment portion including an opening to be optically coupled to the opening of the objective lens attachment portion; (2) a second attachment portion including an opening to be optically coupled to the objective lens; (3) a photodetector for receiving combined light to output a detection signal; (4) a second beam splitter optically coupled to the illumination light source through the opening of the objective lens attachment portion and the opening of the first attachment portion, for splitting light output from the illumination light source into first split light and second split light, irradiating an observation object with the first split light through the objective lens and inputting the first split light reflected by the observation object, inputting the second split light passing through a reference optical path, combining these input first split light and second split light and outputting the combined light to the opening of the first attachment portion and the photodetector; (5) a reference optical system optically coupled to the second beam splitter and provided on the reference optical path, and including a first lens for condensing the second split light output from the second beam splitter, a reference mirror for reflecting the second split light condensed by the first lens to the first lens, and a mirror moving unit for moving the reference mirror in a direction of an optical axis of the first lens; and (6) a housing for holding the first attachment portion, the second attachment portion, the photodetector, the second beam splitter, and the reference optical system.

It is preferable that the interference optical apparatus according to one aspect of the present invention further includes a control unit for obtaining a phase difference in accordance with an optical path difference between the first split light and the second split light from the splitting to the combining in the second beam splitter on the basis of the detection signal, and driving the mirror moving unit on the basis of the obtained phase difference and controlling the optical path difference. It is preferable that the control unit obtains an interference intensity of the combined light on the basis of the detection signal, and adjusts the optical path difference to increase the obtained interference intensity. Further, it is preferable that the control unit obtains an interference intensity of the combined light on the basis of the detection signal, and adjusts a position of the first lens in the direction of the optical axis of the first lens to increase the obtained interference intensity. Further, it is preferable that the control unit adjusts a distance between the objective lens and the observation object and controls a focal position of the objective lens with respect to the observation object.

The interference observation apparatus according to one aspect of the present invention includes a microscope apparatus including an imaging unit for capturing an image of light passing through an objective lens attached to an objective lens attachment portion having an opening; and the above-described interference optical apparatus of the present invention, and the housing of the interference optical apparatus and optical components held by the housing are disposed between the objective lens attachment portion and the objective lens, the objective lens attachment portion and the first attachment portion are optically coupled to each other, and the objective lens and the second attachment portion are optically coupled to each other.

The interference observation method according to one aspect of the present invention includes, in a microscope apparatus including an imaging unit for capturing an image of light passing through an objective lens attached to an objective lens attachment portion having an opening, disposing the above-described interference optical apparatus of the present invention between the objective lens attachment portion and the objective lens, optically coupling the objective lens attachment portion and the first attachment portion to each other, and optically coupling the objective lens and the second attachment portion to each other; obtaining a phase difference in accordance with an optical path difference between the first split light and the second split light from the splitting to the combining in the second beam splitter on the basis of the detection signal, and driving the mirror moving unit on the basis of the obtained phase difference and controlling the optical path difference; and acquiring an interference image using the imaging unit. It is preferable that, in the interference observation method of the present invention, an interference intensity of the combined light is obtained on the basis of the detection signal, and the optical path difference is adjusted to increase the obtained interference intensity. Further, an interference intensity of the combined light may be obtained on the basis of the detection signal, and a position of the first lens in the direction of the optical axis of the first lens may be adjusted to increase the obtained interference intensity. Further, it is preferable that a distance between the objective lens and the observation object is adjusted and a focal position of the objective lens with respect to the observation object is controlled.

INDUSTRIAL APPLICABILITY

One aspect of the present invention is possible to be used as an interference observation apparatus and an interference observation method which can make an optical adjustment easy and acquire an interference image of an observation object with an inexpensive configuration.

REFERENCE SIGNS LIST 1, 1A-1E—interference observation apparatus, 2, 2E—interference optical apparatus, 10—housing, 11—first attachment portion, 12—second attachment portion, 13—light source, 14—photodetector, 15—first beam splitter, 16—second lens, 17—second beam splitter, 21—reference mirror, 22—first lens, 23—drive element (piezo element), 24, 25—stage, 31—control unit, 50—microscope housing, 51—objective lens attachment portion, 52—sample holding table, 53, 54—stage, 55—tube lens, 56—imaging unit, 57—eyepiece lens, 58—illumination light source, 59—beam splitter, 60—splitting optical element, 61—stage, 62—beam splitter, 63—photodetector, 70—objective lens.

The invention claimed is:

1. An interference optical apparatus to be disposed between an objective lens attachment portion and an objective lens in a microscope apparatus including an image sensor configured to capture an image of light passing through the objective lens attached to the objective lens attachment portion having an opening, the interference optical apparatus comprising:
  a first attachment portion including an opening to be optically coupled to the opening of the objective lens attachment portion;
  a second attachment portion including an opening to be optically coupled to the objective lens;
  a light source configured to output light;
  a photodetector configured to receive combined light and output a detection signal;
  a first beam splitter optically coupled to the light source and the photodetector, configured to input the light output from the light source and output the light along a predetermined direction, and input the combined light and output the combined light to the photodetector;
  a second beam splitter optically coupled to the first beam splitter, configured to split the light output from the first beam splitter into first split light and second split light, irradiate an observation object with the first split light through the objective lens and input the first split light reflected by the observation object, input the second split light passing through a reference optical path, combine these input first split light and second split light and output the combined light to the opening of the first attachment portion and the first beam splitter;
  a reference optical system optically coupled to the second beam splitter and provided on the reference optical path, and including a first lens configured to condense the second split light output from the second beam splitter, a reference mirror configured to reflect the second split light condensed by the first lens to the first lens, and a mirror drive element configured to move the reference mirror in a direction of an optical axis of the first lens; and
  a housing configured to hold the first attachment portion, the second attachment portion, the light source, the photodetector, the first beam splitter, the second beam splitter, and the reference optical system.

2. The interference optical apparatus according to claim 1, further comprising a second lens provided on an optical path between the first beam splitter and the second beam splitter, wherein
  in a state where the first attachment portion is optically coupled to the objective lens attachment portion and the objective lens is optically coupled to the second attachment portion, when focus is adjusted such that an imaging plane of the image sensor and the observation object are optically conjugate to each other, the second lens is disposed at a position where a position of the photodetector is optically conjugate to both the imaging plane of the image sensor and the observation object.

3. The interference optical apparatus according to claim 1, wherein the light source is configured to output incoherent light.

4. The interference optical apparatus according to claim 1, wherein the microscope apparatus includes an illumination light source, and wherein
  the second beam splitter is optically coupled to the first beam splitter, optically coupled to the illumination light source through the opening of the objective lens attachment portion and the opening of the first attachment portion, and configured to split both the light output from the first beam splitter and light output from the illumination light source into first split light and second split light, irradiate the observation object with the first split light through the objective lens and input the first split light reflected by the observation object, input the second split light passing through the reference optical path, combine these input first split light and second split light and output the combined light to the opening of the first attachment portion and the first beam splitter.

5. The interference optical apparatus according to claim 1, further comprising:
  a controller configured to obtain a phase difference in accordance with an optical path difference between the first split light and the second split light from the splitting to the combining in the second beam splitter on the basis of the detection signal, and drive the mirror drive element on the basis of the obtained phase difference and control the optical path difference.

6. The interference optical apparatus according to claim 5, wherein the controller is configured to obtain an interference intensity of the combined light on the basis of the detection signal, and adjust the optical path difference to increase the obtained interference intensity.

7. The interference optical apparatus according to claim 5, wherein the controller is configured to obtain an interference intensity of the combined light on the basis of the detection signal, and adjust a position of the first lens in the direction of the optical axis of the first lens to increase the obtained interference intensity.

8. The interference optical apparatus according to claim 5, wherein the controller is configured to adjust a distance between the objective lens and the observation object and control a focal position of the objective lens with respect to the observation object.

9. An interference observation apparatus, comprising:
  a microscope apparatus including an image sensor configured to capture an image of light passing through an objective lens attached to an objective lens attachment portion having an opening; and
  the interference optical apparatus according to claim 1, wherein
  the housing of the interference optical apparatus and optical components held by the housing are disposed between the objective lens attachment portion and the objective lens, the objective lens attachment portion and the first attachment portion are optically coupled to each other, and the objective lens and the second attachment portion are optically coupled to each other.

10. An interference observation method, comprising:
in a microscope apparatus including an image sensor configured to capture an image of light passing through an objective lens attached to an objective lens attachment portion having an opening, disposing the interference optical apparatus according to claim 1 between the objective lens attachment portion and the objective lens, optically coupling the objective lens attachment portion and the first attachment portion to each other, and optically coupling the objective lens and the second attachment portion to each other;
obtaining a phase difference in accordance with an optical path difference between the first split light and the second split light from the splitting to the combining in the second beam splitter on the basis of the detection signal, and driving the mirror drive element on the basis of the obtained phase difference and controlling the optical path difference; and
acquiring an interference image using the image sensor.

11. The interference observation method according to claim 10, wherein an interference intensity of the combined light is obtained on the basis of the detection signal, and the optical path difference is adjusted to increase the obtained interference intensity.

12. The interference observation method according to claim 10, wherein an interference intensity of the combined light is obtained on the basis of the detection signal, and a position of the first lens in the direction of the optical axis of the first lens is adjusted to increase the obtained interference intensity.

13. The interference observation method according to claim 10, wherein a distance between the objective lens and the observation object is adjusted and a focal position of the objective lens with respect to the observation object is controlled.

14. An interference optical apparatus to be disposed between an objective lens attachment portion and an objective lens in a microscope apparatus including an illumination light source, a first beam splitter, and an image sensor configured to capture an image of light passing through the objective lens attached to the objective lens attachment portion having an opening, the interference optical apparatus comprising:
a first attachment portion including an opening to be optically coupled to the opening of the objective lens attachment portion;
a second attachment portion including an opening to be optically coupled to the objective lens;
a photodetector configured to receive combined light and output a detection signal;
a second beam splitter optically coupled to the illumination light source through the first beam splitter, the opening of the objective lens attachment portion and the opening of the first attachment portion, configured to split light output from the illumination light source into first split light and second split light, irradiate an observation object with the first split light through the objective lens and input the first split light reflected by the observation object, input the second split light passing through a reference optical path, combine these input first split light and second split light and output the combined light to the opening of the first attachment portion and the photodetector;
a reference optical system optically coupled to the second beam splitter and provided on the reference optical path, and including a first lens configured to condense the second split light output from the second beam splitter, a reference mirror configured to reflect the second split light condensed by the first lens to the first lens, and a mirror drive element configured to move the reference mirror in a direction of an optical axis of the first lens; and
a housing configured to hold the first attachment portion, the second attachment portion, the photodetector, the second beam splitter, and the reference optical system, wherein
in the microscope apparatus, the first beam splitter is configured to input the light output from the illumination light source and output the light to the second beam splitter, and input the combined light and output the combined light to the image sensor.

15. The interference optical apparatus according to claim 14, further comprising:
a controller configured to obtain a phase difference in accordance with an optical path difference between the first split light and the second split light from the splitting to the combining in the second beam splitter on the basis of the detection signal, and drive the mirror drive element on the basis of the obtained phase difference and control the optical path difference.

16. The interference optical apparatus according to claim 15, wherein the controller is configured to obtain an interference intensity of the combined light on the basis of the detection signal, and adjust the optical path difference to increase the obtained interference intensity.

17. The interference optical apparatus according to claim 15, wherein the controller is configured to obtain an interference intensity of the combined light on the basis of the detection signal, and adjust a position of the first lens in the direction of the optical axis of the first lens to increase the obtained interference intensity.

18. The interference optical apparatus according to claim 15, wherein the controller is configured to adjust a distance between the objective lens and the observation object and control a focal position of the objective lens with respect to the observation object.

19. An interference observation apparatus, comprising:
a microscope apparatus including an image sensor configured to capture an image of light passing through an objective lens attached to an objective lens attachment portion having an opening; and
the interference optical apparatus according to claim 14, wherein
the housing of the interference optical apparatus and optical components held by the housing are disposed between the objective lens attachment portion and the objective lens, the objective lens attachment portion and the first attachment portion are optically coupled to each other, and the objective lens and the second attachment portion are optically coupled to each other.

20. An interference observation method, comprising:
in a microscope apparatus including an image sensor configured to capture an image of light passing through an objective lens attached to an objective lens attachment portion having an opening, disposing the interference optical apparatus according to claim 14 between the objective lens attachment portion and the objective lens, optically coupling the objective lens attachment portion and the first attachment portion to each other, and optically coupling the objective lens and the second attachment portion to each other;

obtaining a phase difference in accordance with an optical path difference between the first split light and the second split light from the splitting to the combining in the second beam splitter on the basis of the detection signal, and driving the mirror drive element on the basis of the obtained phase difference and controlling the optical path difference; and acquiring an interference image using the image sensor.

21. The interference observation method according to claim 20, wherein an interference intensity of the combined light is obtained on the basis of the detection signal, and the optical path difference is adjusted to increase the obtained interference intensity.

22. The interference observation method according to claim 20, wherein an interference intensity of the combined light is obtained on the basis of the detection signal, and a position of the first lens in the direction of the optical axis of the first lens is adjusted to increase the obtained interference intensity.

23. The interference observation method according to claim 20, wherein a distance between the objective lens and the observation object is adjusted and a focal position of the objective lens with respect to the observation object is controlled.

* * * * *